United States Patent
Ringeisen et al.

(10) Patent No.: US 8,133,500 B2
(45) Date of Patent: Mar. 13, 2012

(54) COMPRESSED HIGH DENSITY FIBROUS POLYMERS SUITABLE FOR IMPLANT

(75) Inventors: Timothy A. Ringeisen, Exton, PA (US); W. Christian Wattengel, West Chester, PA (US)

(73) Assignee: Kensey Nash BVF Technology, LLC, Wilmington, DE (US)

( * ) Notice: Subject to any disclaimer, the term of this patent is extended or adjusted under 35 U.S.C. 154(b) by 532 days.

(21) Appl. No.: 10/729,146

(22) Filed: Dec. 4, 2003

(65) Prior Publication Data

US 2005/0123581 A1   Jun. 9, 2005

(51) Int. Cl.
*A61F 13/00* (2006.01)

(52) U.S. Cl. ............ 424/422; 424/423; 424/424

(58) Field of Classification Search ............ 424/422, 424/443, 402, 445, 447, 449, 423, 424; 623/66, 623/16, 20

See application file for complete search history.

(56) References Cited

U.S. PATENT DOCUMENTS

| | | | |
|---|---|---|---|
| 3,616,205 A * | 10/1971 | Ito et al. ............ 435/273 |
| RE29,487 E | 12/1977 | Gardner, Jr. |
| 4,404,033 A | 9/1983 | Steffan |
| 4,501,269 A | 2/1985 | Bagby |
| 4,660,755 A | 4/1987 | Farling et al. |
| 4,902,508 A | 2/1990 | Badylak et al. |
| 4,948,540 A | 8/1990 | Nigam |
| 5,158,574 A * | 10/1992 | Stone ............ 264/108 |
| 5,206,028 A | 4/1993 | Li |
| 5,282,861 A | 2/1994 | Kaplan |
| 5,306,303 A | 4/1994 | Lynch |
| 5,567,806 A | 10/1996 | Abdul-Malak et al. |
| 5,573,784 A | 11/1996 | Badylak et al. |
| 5,702,449 A | 12/1997 | McKay |
| 5,891,558 A | 4/1999 | Bell et al. |
| 5,986,169 A | 11/1999 | Gjunter |
| 5,997,895 A | 12/1999 | Narotam et al. |
| 6,039,762 A | 3/2000 | McKay |
| 6,042,610 A | 3/2000 | Li et al. |
| 6,241,771 B1 | 6/2001 | Gresser et al. |
| 6,346,123 B1 | 2/2002 | McKay |
| 6,371,988 B1 | 4/2002 | Pafford |
| 6,419,945 B1 | 7/2002 | Gresser et al. |
| 6,428,576 B1 * | 8/2002 | Haldimann ............ 623/17.16 |
| 6,503,279 B1 | 1/2003 | Webb |
| 6,548,002 B2 | 4/2003 | Gresser |
| 6,569,201 B2 | 5/2003 | Moumene et al. |
| 6,572,619 B2 | 6/2003 | Santilli |
| 6,599,323 B2 | 7/2003 | Melican et al. |
| 6,613,091 B1 | 9/2003 | Zdeblick et al. |
| 6,974,679 B2 | 12/2005 | Andre et al. |
| 2002/0127270 A1 * | 9/2002 | Li et al. ............ 424/443 |
| 2003/0086975 A1 * | 5/2003 | Ringeisen ............ 424/486 |
| 2004/0258732 A1 | 12/2004 | Shikinami |

FOREIGN PATENT DOCUMENTS

| | | |
|---|---|---|
| DE | 221358 | 4/1985 |
| EP | 0274898 | 7/1988 |
| EP | 0955024 | 11/1999 |
| EP | 1457214 | 9/2004 |
| FR | 2809313 | 11/2001 |
| WO | WO-90/14055 | 11/1990 |
| WO | WO 99/16381 | 4/1999 |
| WO | WO-03/045460 | 6/2003 |
| WO | WO-2004/062531 | 7/2004 |
| WO | WO-2005/056071 | 6/2005 |

OTHER PUBLICATIONS

U.S. Appl. No. 10/601,216, filed Jun. 20, 2003, Ringeisen et al.
Ananthanarayan, V. T., et al., "Development of Fabric Sintering / Compaction Process to Produce Porous UHMW Polyethylene Composites", *J Biomaterials Applications*, vol. 16, (Oct. 2001), 139-148.
Barralet, J. E., et al., "Effect of Porosity Reduction by Compaction on Compressive Strength and Microstructure of Calcium Phosphate Cement", *J Biomedical Materials Research (Applied Biomaterials)*, 63 (1), (Feb. 2002), 1-9.

* cited by examiner

*Primary Examiner* — Michael G Hartley
*Assistant Examiner* — James Rogers
(74) *Attorney, Agent, or Firm* — Jeffrey R. Ramberg

(57) ABSTRACT

An embodiment of the present invention may be made by the following steps: providing a mixture comprising a plurality of fibers, a lubricant, and a suspension fluid, with the suspension fluid filling a void space between said fibers and subjecting said mixture to at least one compressive force. The compressive force causes the migration and alignment of said fibers; and may remove substantially all of the suspension fluid from said mixture. The mixture may further comprise a biologically active agent, or a reinforcing agent.

57 Claims, 13 Drawing Sheets

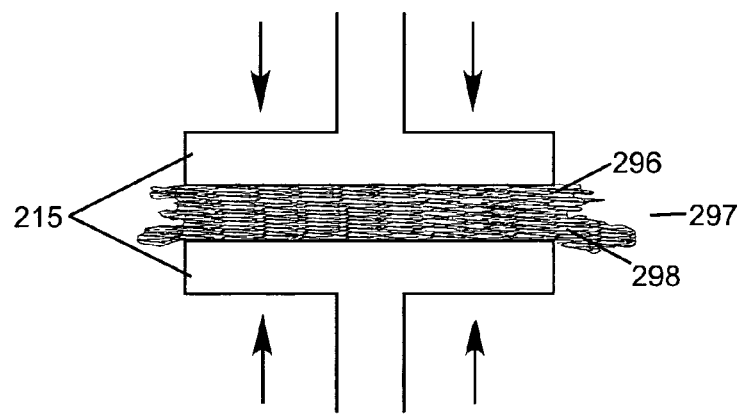
Fig. 2E
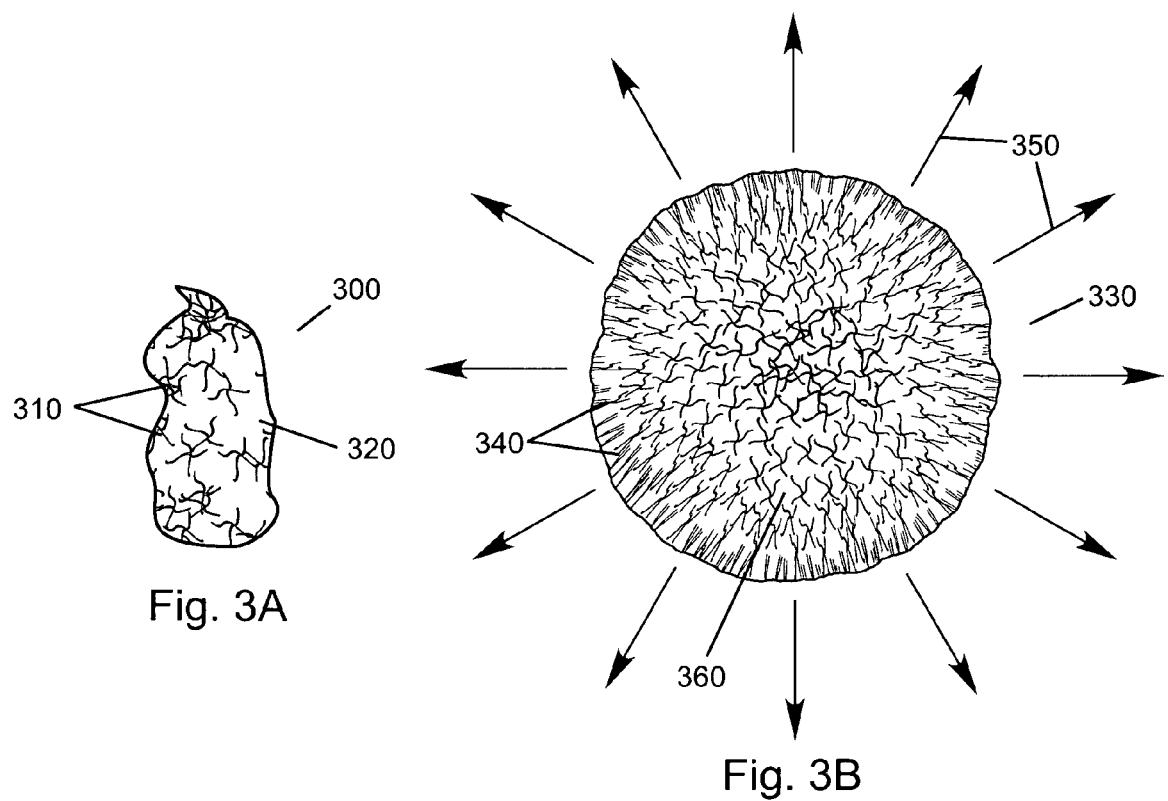
Fig. 3A
Fig. 3B

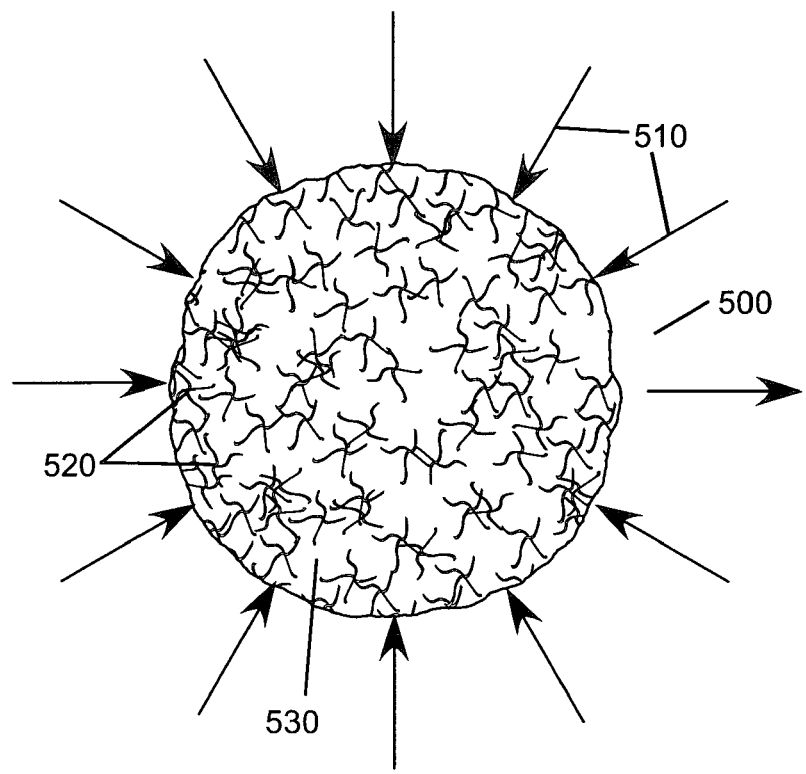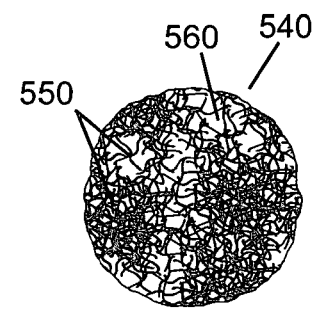
Fig. 5A
Fig. 5B
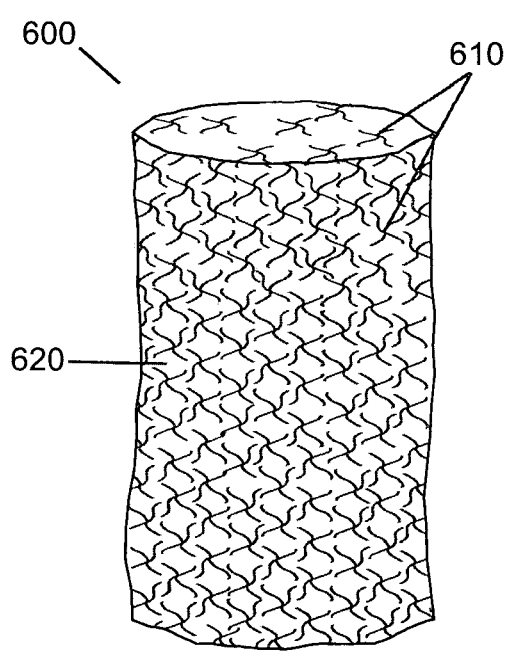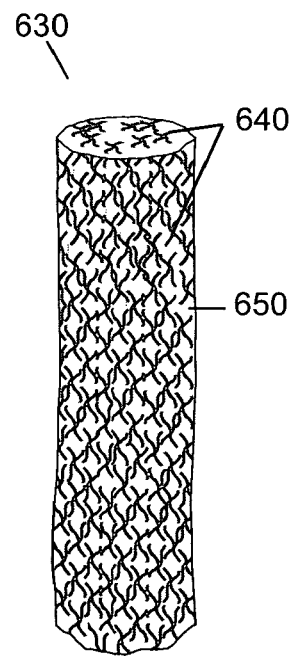
Fig. 6A
Fig. 6B

COMPRESSED HIGH DENSITY FIBROUS POLYMERS SUITABLE FOR IMPLANT

BACKGROUND OF THE INVENTION

Despite the growing sophistication of medical technology, repairing and replacing damaged tissues remains a costly, and serious problem in health care. Currently, implantable prostheses for repairing tissues are made from a wide number of synthetic and natural materials. Ideally, these prosthetic material should be chemically inert, biocompatible, noncarcinogenic, capable of being secured at the desired site, suitably strong to resist mechanical stress, capable of being fabricated in large quantities in the form required, sterilizable, and free of viruses or other contaminating agents. Examples of tissue that can be treated with implantable prostheses include dura mater, tendon (e.g., rotator cuff, anterior cruciate, etc.) and rectic abdominus muscle due to herniation.

A wide variety of prosthetic materials have been used, including tantalum, stainless steel, Dacron, nylon, polypropylene (e.g., Marlex), microporous expanded-polytetrafluoroethylene (e.g., Gore-Tex), dacron reinforced silicone rubber (e.g., Silastic), polyglactin 910 (e.g., Vicryl), polyester (e.g., Mersilene), polyglycolic add (e.g., Dexon), and cross-linked bovine pericardium (e.g., Peri-Guard). To date, no single prosthetic material has gained universal acceptance.

Metallic meshes, for example, are generally inert and resistant to infection, but they are permanent, do not generally adapt in shape as a skeletal structure grows, and they shield the healing tissues from the stresses that may be necessary to generate fully functioning tissue. Non-resorbable synthetic meshes have the advantage of being easily molded and, except for nylon, retain their tensile strength in the body. Their major disadvantages are their lack of inertness to infection, the occasional interference with wound healing, and that they are often long-term implants. Absorbable meshes have the advantage of facilitating tissue in-growth and remodeling at the site of implantation, but often do not have the short-term or long-term mechanical strength necessary for the application.

Both U.S. Pat. No. 4,948,540, granted to Nigam and U.S. Pat. No. 5,206,028 granted to Li, disclose a collagen membrane suitable for medical uses. In the case of Li, the membrane is constructed in a fashion to make it easier for implantation, by ensuring the membrane is not transparent, and not slippery. Both patents begin by providing a solution of collagen, which is freeze-dried, cross-linked, and then compressed. Li then utilizes a second cross-linking, freeze-drying and compression step. The initial cross-linking step locks the fibers into a specific orientation. The compression step merely reduces the porosity within the sheet without inducing fiber migration that would substantially improve the strength of the composition. A second cross-linking step is necessary to hold the sheet in its compressed conformation. What is needed is a sheet with improved strength, capable of maintaining its structural competence without the need of multiple freeze-drying and cross-linking steps.

In U.S. Pat. No. 6,599,524 granted to Li, there is disclosed a membrane sheet having oriented biopolymeric fibers. The membrane is manufactured with oriented parallel fibers formed around a rotating mandrel. The rotations of the mandrel as the fibers are added results in the orientation of the fibers. The membrane is then compressed to drive out excess liquid, and cross-linked, resulting in a membrane with directionally oriented fibers. This material is only aligned in a single direction and must be laminated with binding agents in order to create a functional device. Additionally, such a device does not provide gradients such as those seen in natural tissues. What is needed is a method that allows for layering that occurs at the microscopic as well as the macroscopic level as part of a one step process and more closely represents the layered structure of natural connective tissues.

Prosthetic devices are used in the repair, augmentation, or replacement of articulating organs. For example, the rotator cuff (i.e., shoulder joint) is made up by a combination of the distal tendinous portion of four muscles: the supraspinatus, subspinatus, subscapularis and the teres minor. Proper functioning of this tendonous cuff, depends on the fundamental centering and stabilizing role of the humeral head with respect to sliding action during lifting and rotation movements of the arm. A tear in the rotator cuff tendons is a common injury that can be caused by constant friction from repetitive overhead motion, trauma, or age-related degeneration that can narrow the space between the clavicle and the top of the scapula.

To repair large tears of the rotator cuff, it is desirable to use a scaffold or graft material to help support the damaged tissue and guide its repair. Several types of materials have been used for such procedures. Wright Medical (Memphis, Tenn.) markets a product known as GraftJacket, which is manufactured by Lifecell Corporation (Branchburg, N.J.) from human cadaver skin. Human cadaverous tissue products can be difficult to obtain and have the potential for disease transmission. Tissue Sciences (Covington, Ga.) markets a product known as Permacol, which is comprised of cross-linked porcine dermis. DePuy (Warsaw, Ind.) markets the Restore Patch which is fabricated from porcine small intestine submucosa. Biomet (Warsaw, Ind.) markets a product known as CuffPatch another porcine small intestine product. The CuffPatch and the Restore Patch products provide biocompatible scaffolds for wound repair but they are complicated to manufacture, as they require the lamination of multiple layers of submucosal tissues to gain the strength needed for these applications. Fabrication of such patches from porcine small intestine submucosa are described in U.S. Pat. No. 4,902,508 Badylak et al. and U.S. Pat. No. 5,573,784 Badylak et al.

Additional applications for prosthetic devices exist in the form of membrane patches. The spinal cord and brain are covered with a protective membrane that is known as the dura mater. The integrity of the dura mater is critical to the normal operation of the central nervous system. When this integrity is intentionally or accidentally compromised (e.g., ruptured, severed, damaged, etc.), serious consequences may ensue, unless the membrane can be repaired. Typically, dura tissue is slow to heal. To enhance the healing process, graft materials can be utilized to guide the regeneration of the tissue. Repairing damaged membranes has largely focused on implantable materials known as dural substitutes, which are grafted over the damaged dura mater and are designed to replace and/or regenerate the damaged tissue.

Thus, there is a need for an effective dura substitute that would be biocompatible, sufficiently noninfectious (e.g., purified, etc.) to prevent the transmission of disease, conformable, available in a variety of sizes, high in tensile strength, inert, suturable, and optionally capable of forming a water-tight seal.

Researchers have experimented with a wide variety of substances to act as dura substitutes. Autologous grafts of tissue, such as pericardium, can be effective as a dura substitutes; however, autologous tissue is not always available and it posses additional costs and risks for the patient. Cadaverous dura mater has also been used but like autologous tissues, cadaverous tissues can be difficult to obtain. Tutogen Medical Inc. (West Paterson, N.J.) markets a product known as Tutoplast dura mater, which is obtained from human cadavers. Processed human cadaveric dura mater has been implicated in the transmission of cases of the fatal Creutzfeldt-Jakob disease. Other products overcome this shortcoming by using alternate materials. The Preclude Dura substitute, manufactured by W. L. Gore (Newark, Del.), is an inert elastomeric fluoropolymer material. The material is biocompatible but is a permanent implant and does not resorb over time. Dural substitutes comprising collagen have been also been explored as described in U.S. Pat. No. 5,997,895 (Narotam et al.). Integra Lifesciences Corporations (Plainsboro, N.J.) distributes a product known as DuraGen. The product is manufactured from bovine achilles tendon and is a pliable porous sheet. Although the material is resorbable and biocompatible, the integrity of the material is not sufficient enough to withstand suturing to the wound site.

The present invention overcomes these suturing and other difficulties of the materials currently available and provides a structure capable of being adapted to a wide variety of surgical applications.

Other applications for the implantable prosthesis of this invention, in the form of a surgical mesh, include pelvic floor disorders such uterine and vaginal vault prolapse. These disorders typically result from weakness or damage to normal pelvic support systems. The most common etiologies include childbearing, removal of the uterus, connective tissue defects, prolonged heavy physical labor and postmenopausal atrophy. Many patients suffering from vaginal vault prolapse also require a surgical procedure to correct stress urinary incontinence that is either symptomatic or latent.

Another embodiment of the present invention is directed to devices useful as prosthetic menisci, and in vivo or ex vivo scaffolds for regeneration of meniscal tissue.

The medial and lateral menisci are a pair of cartilaginous structures in the knee joint which together act as a stabilizer, a force distributor, and a lubricant in the area of contact between the tibia and femur. Damaged or degraded menisci can cause stress concentrations in the knee thereby creating abnormal joint mechanics and leading to premature development of arthritic changes.

In the prior art, treatment of injured or diseased menisci has generally been both by surgical repair and by tissue removal (i.e., excision). With excision, regeneration of meniscal tissue may not always occur. Allografting or meniscal transplantation is another method of replacement, which has been previously tried.

This approach has been only partially successful over the long term due to the host's immunologic response to the graft and to failures in cryopreservation and other processes. Alternately, menisci have been replaced with permanent artificial prostheses such as Teflon and polyurethane. Such prostheses have been selected to be inert, biocompatible, and structurally sound to withstand the high loads which are encountered in the knee joint. Typically, these permanent implants do little to encourage the regeneration of the damaged host tissue. Therefore, what is needed is an improved prosthetic meniscus composed of biocompatible materials, which are biocompatible, compliant, durable, and suitable to acts as a temporary scaffold for meniscal fibrocartilage infiltration and regeneration of the host tissue.

In U.S. Pat. No. 5,184,574 granted to Stone and U.S. Pat. No. 6,042,610 granted to Li, there is disclosed a meniscus replacement material, manufactured by shape molding collagen fibers within a mold via application of low pressure by a piston prior to or after drying. Stone requires the step of applying freezing cycles to the material. The fibrous materials achieve densities of 0.07-0.5 g/cc. Hydrated fibers at these density range from a free flowing liquid slurry to a loose dough-like material unable to maintain a shape. Freezing and possibly lyophilizing of the material is necessary to remove it from the mold and cross-linking solutions are applied to it while still in the frozen or lyophilized state so that it does not warp. Fiber orientation may be obtained by applying a rotating force to the piston in order to form a circumferential orientation. However, this orientation occurs only in areas directly in contact with the rotating piston. What is necessary is a fibrous construct with sufficient integrity to be handled without the necessity of freezing and/or lyophilizing and that can be implanted without the requirement of cross-linking, if desired. Additionally, this construct lacks any consistency throughout the thickness of its structure, being able to create oriented fibers only at the periphery.

Another embodiment of the present invention is directed to devices useful as prosthetic ligament, and in vivo or ex vivo scaffold for regeneration of ligament tissue and to methods for their fabrication.

The anterior cruciate ligament (ACL) of the knee functions to resist anterior displacement of the tibia from the femur during flexure. The ACL also resists hyperextension and serves to stabilize the fully extended knee during internal and external tibial rotation. Partial or complete tears of the ACL are common. The preferred treatment of the torn ACL is ligament reconstruction, using a bone-ligament-bone autograft (e.g., from the patient's patellar tendon or hamstring tendon). Cruciate ligament reconstruction generally provides immediate stability and a potential for immediate vigorous rehabilitation. However, ACL reconstruction is not ideal; the placement of intraarticular hardware is required for ligament fixation; anterior knee pain frequently occurs, and there is an increased risk of degenerative arthritis with intraarticular ACL reconstruction. Another method of treating ACL injuries involves suturing the torn structure back into place.

This repair method has the potential advantages of a limited arthroscopic approach and minimal disruption of normal anatomy. A disadvantage of this type of repair is that there is generally not a high success rate for regeneration of the damaged tissues due to the lack of a scaffold or other cellular inductive implant.

Another embodiment of the present invention relates to devices useful as a prosthetic intervertebral disc. The intervertebral disc plays an important role in stabilizing the spine and distributing the forces between the vertebral bodies. In the case of a damaged, degenerated, or removed disc, the intervertebral space collapses over time and leads to abnormal joint mechanics and premature development of arthritis.

In the prior art, discs have been replaced with prostheses composed of artificial materials. The use of purely artificial materials in the spine minimizes the possibility of an immunological response. Such materials must withstand high and repeated loads seen by the spinal vertebral joints, early attempts focused upon metallic disc implants. These efforts met with failure due to continued collapse of the disc space and or erosion of the metal prosthesis into the adjacent bone.

SUMMARY OF THE INVENTION

The current invention is directed to a general prosthesis, which, when implanted into a mammalian host, undergoes controlled biodegradation accompanied by adequate living cell replacement, such that the original implanted prosthesis is remodeled by the host's cells before it is degraded by the host's enzymes and/or by hydrolosis. The device of the subject invention is structurally stable, pliable, semi-permeable, and suturable.

Embodiments of this invention can be utilized to repair, augment, or replace diseased or damaged organs, such as rotator cuff injuries, dura defects, abdominal wall defects, pericardium, hernias, and various other organs and structures including, but not limited to, bone, periosteum, perichondrium, intervertebral disc, articular cartilage, dermis, epidermis, bowel, ligaments, tendon, vascular or intra-cardiac patch, or as a replacement heart valve.

The device if this invention could be used for sling procedures (e.g., surgical methods that place a sling to stabilize or support the bladder neck or urethra). Slings are typically used to treat incontinence. Additionally, in the form of a surgical mesh, the device can be used for such applications as hernia and dura repair.

In another embodiment, this invention provides a ligament repair or replacement prosthesis that is biocompatible, is able to withstand ACL forces, and promotes healing of the injured tissues by acting as a scaffold for cellular infiltration. Another embodiment of this invention is to provide an improved disc replacement or prosthesis that is biocompatible, does not interfere with normal vertebral segment motion, is able to withstand normal spinal column forces, does not wear into the surrounding bone, promotes regrowth of intervertebral disc material and acts as a scaffold for fibrocartilage infiltration.

The tissue repair implant of this invention, functioning as a substitute body part, may be flat, tubular, hollow, solid, or of complex geometry depending upon the intended use. Thus, when forming the structure of the prosthesis of this invention, a mold or plate can be fashioned to accommodate the desired shape.

Flat sheets may be used, for example, to support prolapsed or hypermobile organs by using the sheet as a sling for those organs or tissues (e.g., bladder or uterus). Tubular grafts may be used, for example, to replace cross sections of tubular organs such as esophagus, trachea, intestine, and fallopian tubes. These organs have a basic tubular shape with an outer surface and a luminal surface. In addition, flat sheets and tubular structures can be formed together to form a complex structure to replace or augment cardiac or venous valves and other biological tissue structures.

The tissue repair implant of the present invention may be rendered porous to permit the in-growth of host cells for remodeling or for deposition of the collagenous layer. The device can be rendered "non-porous" to prevent the passage of fluids if necessary or the porosity can be adjusted to create a membrane capable of selective permeability. The degree of porosity will affect mechanical properties of the implant, and these properties are also affected by processing (as will be discussed).

The mechanical properties include mechanical integrity such that the tissue repair implant resists creep for the necessary period of time, and additionally is pliable (e.g., has good handling properties) and suturable. The term "suturable" means that the mechanical properties of the layer include suture retention, which permits needles and suture materials to pass through the prosthesis material at the time of suturing of the prosthesis to sections of native tissue. During suturing, such prostheses must not tear as a result of the tensile forces applied to them by the suture, nor should they tear when the suture is knotted. Suturability of tissue repair implant, i.e., the ability of prostheses to resist tearing while being sutured, is related to the intrinsic mechanical strength of the prosthesis material, the thickness of the prosthesis, and the tension applied to the suture. The mechanical integrity of the prosthesis of this invention is also in its ability to be draped or folded, as well as the ability to cut or trim or otherwise shape the prosthesis.

In another embodiment of the invention, reinforcing elements (e.g., threads, fibers, whiskers, textiles, etc.) are incorporated into the tissue repair implant for reinforcement or for different rates of remodeling. Thus, the properties of the tissue repair device can be varied by the geometry of the thread used for the reinforcement. Additionally thread constructs such as a felt, a flat knitted or woven fabric, or a three-dimensional knitted, woven or braided fabric may be incorporated between layers or on the surface of the construct. Porous, non-fibrous sheets of polymer foam may also be incorporated between layers or on the surface of the construct. Such polymer foams can be made by methods known in the art such as particulate leaching or solvent freeze-drying methods.

An embodiment of the present invention may be made by the following steps: providing a mixture comprising a plurality of fibers, a lubricant, and a suspension fluid, with the suspension fluid filling a void space between said fibers and subjecting said mixture to at least one compressive force. The compressive force causes the migration and alignment of said fibers; and may remove substantially all of the suspension fluid from said mixture. The mixture may further comprise a biologically active agent, or a reinforcing agent.

Additionally, the compressive forces may reduce the void space between the fibers, and the lubricant may assist fiber movement during compression, and be in the form of a liquid or a solid, and may be provided in a carrier fluid. The suspension fluid flow may also cause plates of oriented fibers to be formed.

The compressive force may be applied by a molding surface, thereby creating a shaped fibrous member in said mold. Additionally, or alternatively, the material may be machined, allowing the fabrication of complicated shapes.

In a preferred embodiment, at least a portion of said compressed mixture may be cross-linked by exposure to a cross-linking agent. This process will affect the strength and resorption rate of the implant. Additionally, the strength may be tailored by a reinforcing element, such as particulates, threads, fibers, whiskers, textiles, rods, meshes, or combinations thereof. The function or properties of the implant may also be affected by additives, such as ceramics, polymers, cells, biologically active agents, liquids, surfactants, plasticizers, and combinations thereof.

DESCRIPTION OF THE DRAWINGS

FIG. 3 depicts fibrous dough prior to and after compression.

FIG. 5 depicts three-dimensional compression of fibrous dough.

FIG. 6 depicts compression of a cylindrical mass of fibrous dough.

DETAILED DESCRIPTION OF PREFERRED EMBODIMENTS

Figure 1A:
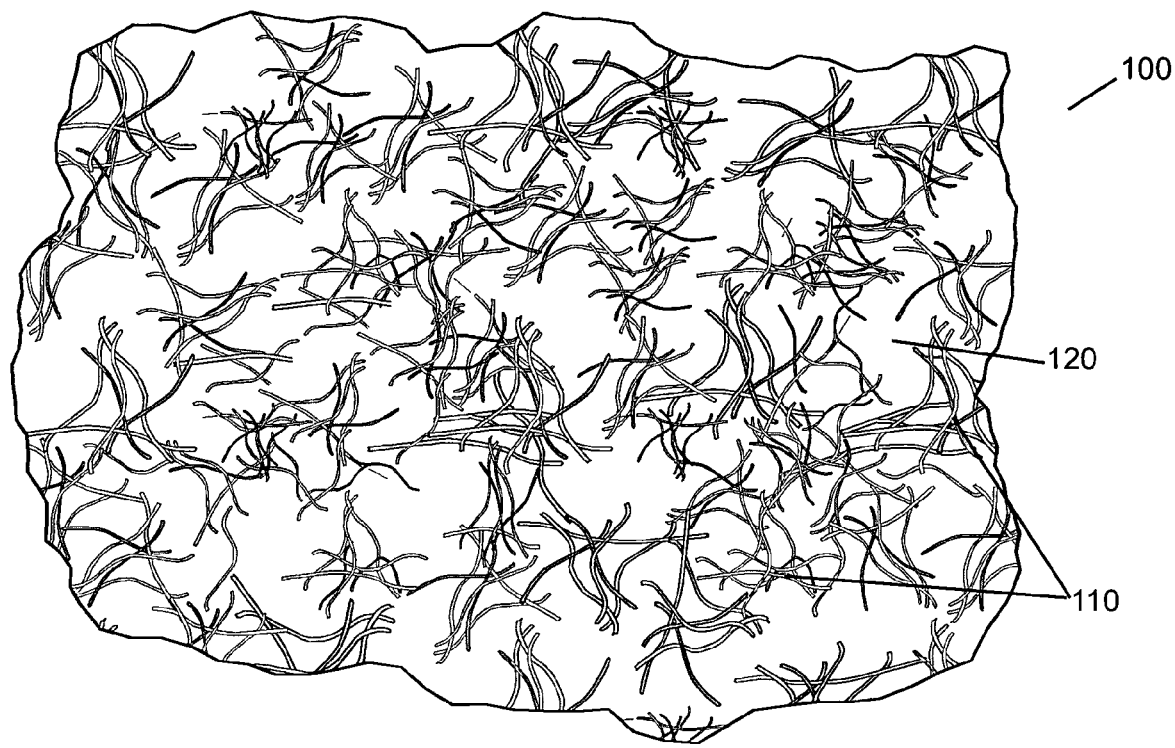
FIG. 1 depicts fibrous dough prior to and after compression.

Embodiments of this invention include compressed, biodegradable, fibrous compositions for application to a tissue site in order to support, promote or facilitate new tissue growth. One aspect of this invention is a fibrous component (e.g., collagen, elastin, chitosan, alginate, hyaluronic acid, polyglycolic acid, polyurethane, silk, etc.; see table 1) that provides unique mechanical and physical properties, as will be discussed. Such fibrous components in slurry form may be pre-processed into a fibrous dough or paste by removal of a portion of suspension fluid, as known in the art, prior to formation into a compressed conformation, as will be disclosed. An example is in the form of an interlaced matrix described in U.S. patent application Ser. No. 10/601,216 filed on Jun. 20, 2003 and assigned to the same assignee of the present invention, which is incorporated by reference herein. The material is a natively cross-linked collagen such as Semed F produced by Kensey Nash Corporation (Exton, Pa.).

The fibrous dough is dehydrated/desolvated by applying a compressive force in such a manner as to reduce the inter fiber space by removing at least a portion of the suspension fluid. The compression is unconstrained in directions lateral to the direction of compression. In a preferred embodiment substantially all of the suspension fluid is removed. Unlike unaltered or natural matrices (e.g., dermis, small intestine submucosa, etc.), the thickness, porosity, fiber-density, fiber-orientation, fiber-length, fiber composition and component-ratio (e.g., Collagen to Elastin ratio), as a non-limiting example, can be controlled with the current invention.

To improve the migration of fibers and prevent clumping during the compressive process it is preferred to incorporate a percentage (e.g., 0%-50% by mass of fibers) of one or more lubricants (e.g., biocompatible oils, hydrogels, liquid polymers, low-molecular weight polymers, glycosaminoglycans, surfactants, waxes, fatty acids, fatty acid amines and metallic stearates such as zinc, calcium, magnesium, lead and lithium stearate, etc.) into the fibrous dough suspension. A lubricant is defined as a substance, which is capable of making surfaces smooth or slippery. These characteristics are due to a reduction in friction between the polymers to improve flow characteristics and enhance the knitting and wetting properties of compounds. Said lubricant may be liquid or solid and may be suspended or dissolved in a carrier solvent (e.g., water, alcohol, acetone, etc.). Additionally the lubricant may only become lubricious under compressive force or change in temperature. The lubricant may remain in its entirety in the final invention; may be partially removed in the dehydration/desolvation process; or, may be washed out or removed by methods known in the art during further processing. Lubricants that remain in the final invention may be biologically active agents or may form microstructures. Preferred lubricants include Tween-80, hyaluronic acid, alginate, glycerin or soluble collagen with the most preferred being acid soluble collagen such as Semed S produced by Kensey Nash Corporation (Exton, Pa.).

Additional ways in which to add lubricity include physically or chemically altering the surface of the fibers making up the composition. Such alterations can be achieved through chemical or physical attachment of a lubricious substance to the fibers, temperature induced phase changes to the surfaces of the fibers or partial solubilization of the fibers through alteration of the pH and/or conductivity of the free fluid or use of a percentage of solvent for the fibers within the free fluid. Other methods of creating lubricity are known to those skilled in the art, and are embraced by this disclosure.

During the compression step of the fibrous dough, the fibers align themselves into layered or plate-like structures. As the inter fiber void space is collapsed, the displaced fluid is forced outward and begins to flow out of the device. The flow may play a role in aligning the fibers in that direction. The rate of flow is directly affected by rate and duration at which compression occurs. This phenomenon occurs throughout the structure and results in aligned fibrous layers or plates separated by fluid planes. These planes facilitate migration within the structure, allowing the fibers within a single layer to move without interference from fibers in a different layer.

The compression induced fluid migration may occur three-dimensionally, thereby dissecting planes in the structure as it runs into resistance. Additionally the fluid may be forced through narrow passageways in the fibrous mats and begin creation of a new plane at a different level within the construct. Thus it is possible to create a structure wherein the planes do not traverse the entire length of the device, but instead exist as multiple fissures located randomly within the construct and each fissure can be defined by fibrous plates having an aligned fiber orientation unique from that of neighboring fissures. The plates themselves may be organized in a random, oriented, or aligned fashion. As compression continues, the lubricant reduces the friction, allowing the aligned fibers within the plates or planes to slide across each other and nest in the most compact orientation. Additional compression brings the plates of fibers in closer contact, allowing them to become locked into a compact anisotropic structure, although the material may be isotropic in two dimensions.

Unlike existing state of the art sheets, this layering occurs at the microscopic as well as the macroscopic level as part of a one step process and more closely represents the layered structure of natural connective tissues. Additionally, the amount of fiber compaction within a plate or layer and the spacing between the plates or layers can be controlled by the force applied and the amount of time allowed for equilibration at a specific force. The preferred force applied is from 0.01 tons/square inch to 100 tons/square inch with the most preferred force being in the range of 0.2 tons/square inch to 2.0 tons/square inch. This amount of force is in excess of state of the art methods used merely to extract fluid and concentrate the fibers into workable dough-like material. Existing methods do not induce fiber migration or layer formation. Devices created under such conditions as described above do not require additional steps such as freezing and/or cross-linking within molds to be handled. The preferred amount of equilibration time is in the range of about less than one minute to more than 500 minutes with a more preferred range of about 1 minute to 60 minutes.

The use of wicking materials such as paper towels/sponges or fluid removal systems such as screens or vacuum systems prevent excessive pooling of fluid in any single area of the structure during compression. If fluid is allowed to accumulate, it can create craters or voids within the structure. If the fibers surround these pools of fluid succumb to the compressive forces, a rip or discontinuity in the structure will form as the fluid is forcibly expelled. Strategic location of fluid exit pores within a mold can be used to create unique directional flows that in turn align the fibers within a layer or plate. In this way the fibers forming plates at each level can be oriented in the same direction or turned at any conceivable angle to each other. Although orientation of fibers from plate to plate may be organized or random, fiber orientation within a plate is organized with the fibers running predominantly parallel to each other. Molds with fluid vacuum assist further improve control of fiber orientation. Additionally, materials such as threads and screens provide avenues for fluid escape. As the fluid flows along the length of the threads and screens, the fibers adjacent to them are aligned parallel to them. Use of porous rods or porous hollow tubes that can be extracted or left in place as reinforcement can also be used to facilitate uniform fluid removal. If the fluid extraction tubes are removed, long channels will be left that can be utilized for purposes such as suture line conduits.

As the inter fiber space is reduced and the free fluid within the dough is expelled, the overall porosity of the compressed composition is reduced towards a theoretical zero point. The amount of porosity as well as the size of the pores dictates whether the device functions as a tissue matrix or barrier. Additionally, the physical/mechanical properties are highly influenced by the amount of inter fiber space. Another factor affecting the mechanical and physical properties of the composition is the use of additives (e.g., surfactants, plasticizers, particulates, porosifiers, meshes, etc.).

In a preferred embodiment, the method of preparing the high-density fibrous matrix involves: providing a fibrous material; contacting said fibrous material with a suspension fluid and a lubricant; applying a compressive force within one or more dimensions that partially dehydrates/desolvates the fibrous material. Subsequently, the fibrous material may be cross-linked. It may be further desirable to provide a directed means of egress for the suspension fluid during compression, as previously discussed. Additionally use of a fibrous suspension having interlaced, interlocked fibers may be desirable.

In another embodiment, the partially dehydrated fibrous matrix is fully dried (e.g. vacuum dried, freeze-dried, air-dried.) after which it may be cross-linked. It may be further desirable to rehydrate/resolvate the fibrous matrix to facilitate incorporation of cross-linking agents, plasitisizers, surfactants, biologically active agents, microstructures, cells or other materials. If desired the sheet may again be dried.

Any method of compression known by those skilled in the art is conceivable for this invention, including, but not limited to, using hydraulically or pneumatically powered platens or pistons to compress the fibrous matrix material. Other methods include but are not limited to using a screw or an arbor press to compress the material, using centrifugation to extract fluid and compress the fibers, or forcing the material between rollers.

The structure of the fibrous matrix material is also influenced by the amount of compressive force applied to the material. The amount of compression may change the porosity of the fibrous matrix material. The pore size distribution will also be affected by the amount of compression as the fibrous matrix material may be compressed so that only certain areas have collapsed, or so that all areas collapse. The direction of compression in relationship to the original structure of the fibrous matrix material will also affect the structure of the compressed fibrous matrix material. For example, if the initial fibrous matrix material has long parallel fibers, a force applied could be used to force the fibers together in a parallel fashion or bunch up the fibers as the force attempts to shorten the length of the fibrous composition.

Compression of the fibrous matrix material can be controlled to create various structural patterns within the material; likewise, the mechanical properties of the material may be altered to meet specific requirements. The amount of compression is directly related to the tear strength of the material. If a medical device fabricated from the compressed material is not in the form of a sheet, the compressed material can be compressed three-dimensionally to form the desired shape. If the medical device is axially loaded, the compressed material may be compressed in one direction to optimize the mechanical properties of the material in that direction.

If not compressed initially into the final shape, after being compressed and removed from the compression device, the fibrous matrix material may be machined into a new shape or design with various features. Machining processes are well known to those skilled in the art. (e.g., punching, coring, milling, sawing, lathing, etc.) Additionally, the compressed fibrous matrix may function as a component of a larger device and if not attached during the compression step, may be attached to components by methods known to those in the art (e.g., gluing, stapling, sewing, etc.).

The inventors have discovered that after the compressive dehydration/desolvation process the resultant material has mechanical properties, including tear strength, superior to those of non-compressed materials that have been cross-linked. Not being confined to a single theory, it is believed that the high compressive forces will create weak chemical linkages aside from the physical interaction of the fibers. This permits the current invention to be utilized in applications that initially require specific tear strength but where it is desirable for the device to be quickly degraded away after fulfilling its initial function such as dura repair. The current invention can be cross-linked, either chemically (e.g., EDC) or by non-chemical methods (e.g., dehydrothermal (DHT)) know to those skilled in the art, for applications requiring strength for an extended period of time, such as hernia repair.

The inventors have further discovered that a non-compressed or mildly compressed sheet can be cross-linked, completely or only at the surface, by a first method after which it is fully compressed and cross-linked by a second method. The first cross-linking restricts motion of the fibers during the compression step, retarding an increase in the footprint of the sheet. Even thought the sheet is cross-linked in the non-compressed state, the addition of a lubricant facilitates migration and shifting of the partitions making up the sheet. This allows thick sheets to achieve the same fiber density per unit volume as thin sheets.

Highly compressed sheets of collagen fibers placed into cross-linking solutions have formed a tough cross-linked skin around a minimally non-cross-linked center. The center of such sheets are easily separated forming a shell, pocket or bladder. The permeability of the bladders varied depending upon the initial compression. Low compression produced bladders that slowly allowed dyed fluid to exude. Moderate compression allowed water to pass through but filtered out the larger dye molecules. High compression created a barrier to fluid water but slowly allowed the escape of water vapor. Such a phenomenon was not evident in DHT cross-linked sheets.

Such devices would be useful for tissue engineering applications associated with bladder, intestine, tendons, ligaments and vessels, as well as the creation of rotator cuff patches, hernia repair sheets, orbital implant coverings, graft wraps and the formation of anti-adhesion devices. The shell of material could be filled with ceramics or polymers useful in bone repair or used as containment devices for injection of settable polymers or ceramics. Additionally, the center could be filled with fluids prior to or after implantation for applications such as controlled drug delivery or the creation of shock absorbing vessels useful for breast implants, fat pad replacement or meniscus and disc repair or replacement.

Restricted contact of cross-linking solutions with the surfaces of collagen devices control the degree of cross-linking in fibrous, non-fibrous, compressed and non-compressed materials. For example, restricted contact can be achieved by placing shaped, fully hydrated, collagen dough into a cross-linking solution. The cross-linking solution slowly displaces hydration fluid at the periphery but does not immediately come into contact with the hydrated material in the center. As the material continues to sit in the cross-linking solution a gradient begins to form with a greater amount of cross-linking occurring at the surface and lesser amounts of cross-linking occurring toward the center.

Additionally, a second type of cross-linking could be introduced after drying to create a bi-phasic cross-linking (e.g., DHT, chemical vapors, radiation). Devices having such unique cross-linkings would be useful in tissue-engineering applications involving multi-phasic tissues such as cartilage and skin or could function as in-vivo cell culture vessels capable of protecting foreign cells, such as islet cells from a different person or animal, from attack by the recipients' immune system.

The central portion of units cut from compressed collagen sheets having only the surface cross-linked swell when in contact with excess aqueous fluids. A small amount of fluid hydrates the sheet and creates thin flexible units. Only after being placed in contact with excess fluid does the sheet begin to swell. The swelling can be delayed by minutes to hours depending upon the initial thickness, magnitude of compression, and the amount of cross-linking at the surface. This creates a large central porosity suitable for cell migration and/or delayed drug or biologics delivery, centered between two low-porosity protective sheets. Such a device would also be suitable in applications requiring implantation through a small opening that will swell to full size after becoming fully hydrated by body fluids.

The fibrous matrix material may be compression molded into an initial or final design of a medical device. If the device has complicated geometry, various features may be machined after compression molding. The material and mechanical properties of the final device can be altered by the temperature of the molds, the amount of overall compression, the design of the mold, etc. The fibrous matrix material may be compressed before molding, or all the compression may occur during the molding process. The direction of compression before or during compression molding will also affect the mechanical properties of the device. For example, a cylinder of fibrous dough material may be three-dimensionally compressed to improve the mechanical properties and then compression molded into a threaded bone screw. Additionally, the cylinder of fibrous material could be compressed into a cone shape providing a gradient of compression. Such gradients would be useful for multi-phasic tissue or multi-phasic drug delivery.

The implantable prosthesis of the present invention may be sterilized by any method known in the art. (e.g., exposure to ethylene oxide, hydrogen peroxide gas plasma, e-beam irradiation, gamma irradiation, etc.) The sterilization minimizes the opportunity of infection to occur as a result of the implant.

In the preferred embodiment of the invention, the fibrous prosthesis is manufactured from a resorbable material, although this is not meant to exclude the use of non-resorbable polymers, minerals and metals within the final structure.

Different polymers, molecular weights, additives, processing methods, cross-linking methods and sterilization methods can be used to control the resorption rates of resorbable polymers and is well know by those skilled in the art. For example, reconstituted collagen fibers degrade faster than natively cross-linked collagen fibers and collagen that has not been cross-linked degrades faster than cross-linked collagen. Additives such as ceramics capable of increasing the localized pH also increase the rate of degradation, as do chemotactic ground substances that attract cells to the localized area. Resorption rates can be adjusted to be shorter for applications that require mechanical strength for only a short period of time or longer for applications that require mechanical strength to be present for a longer duration. Examples of resorbable polymers that can be formed into fibers and used to form the prosthesis are shown in Table 1. These materials are only representative of the materials and combinations of materials that can be used as prosthetic material and this table is not meant to be limiting in any way.

For the purposes of promoting an understanding of the principles of this invention, reference will now be made to the embodiments illustrated in the drawings and specific language will be used to describe the embodiments and elements of the embodiments. It must be understood that no limitation of the scope or applications of the invention is thereby intended. For ease of understanding, fibers are represented in the drawings by simple crossed lines, by no way does this indicate that they may not be interconnected, interwoven, interlaced or entangled, or that the final structure is porous or non-porous, organized or random, and/or reticulated, except as otherwise noted. In theory, the compressed fibrous structure could in fact be produced through the compression of a single continuous fiber.

Figure 1B:
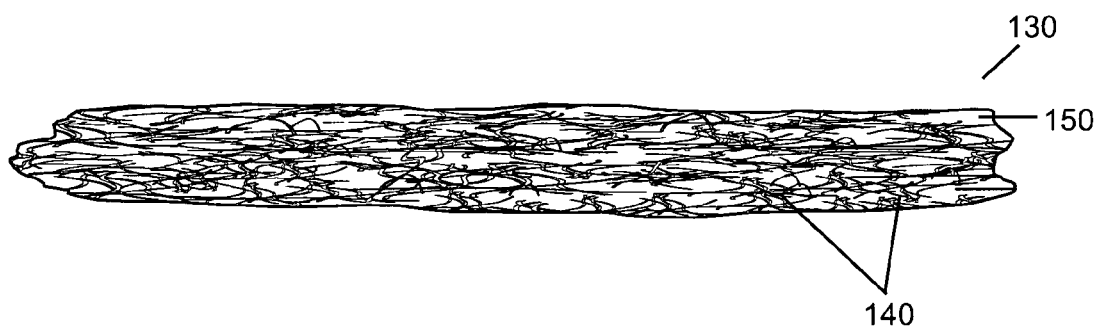

Referring now to the drawings, FIG. 1 shows the fibrous matrix material before and after compression. Before compression, shown in FIG. 1A, the fibrous matrix material 100 comprises a large percentage of void space surrounding the fibers 110. The fibers 110 form a structure composed mostly of inter fiber void space 120. After being compressed, shown in FIG. 1B the compressed porous matrix material 130 contains the same amount of fibrous material 140; however, the sacrificed, inter fiber void space 150 has resulted in a reduced porosity in the material. It should be noted that the inter fiber void space in this figure and all other figures may contain a lubricant as has been discussed.

Figure 2A:
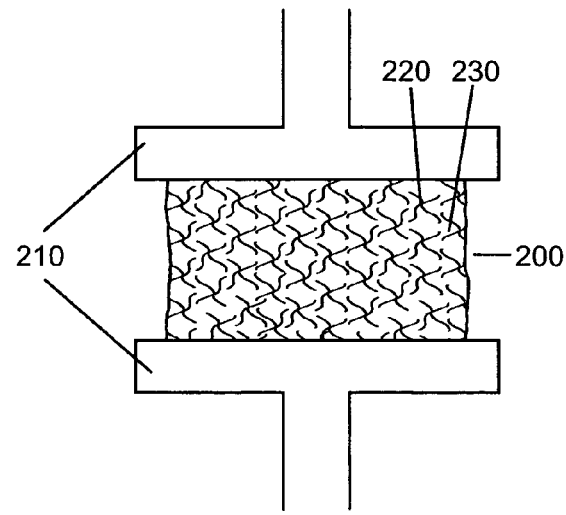
FIG. 2 depicts a change in fiber orientation and inter-fiber void space as the fibrous dough is compressed.
Figure 2B:
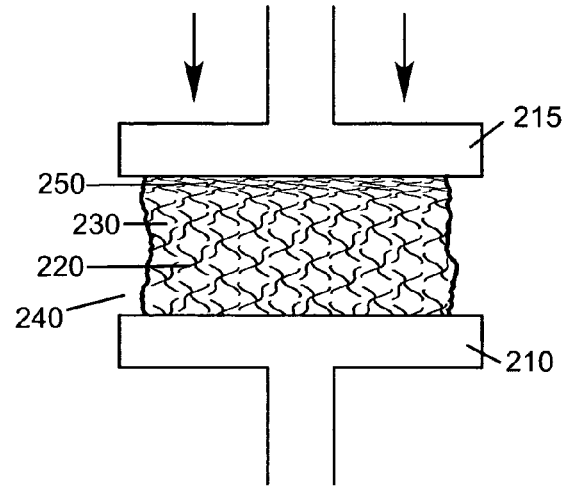
Figure 2C:
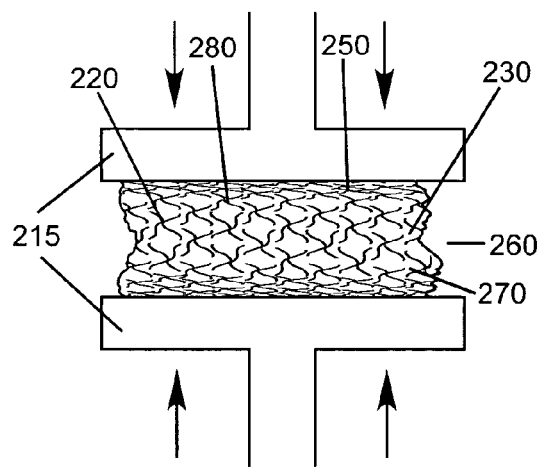
Figure 2D:
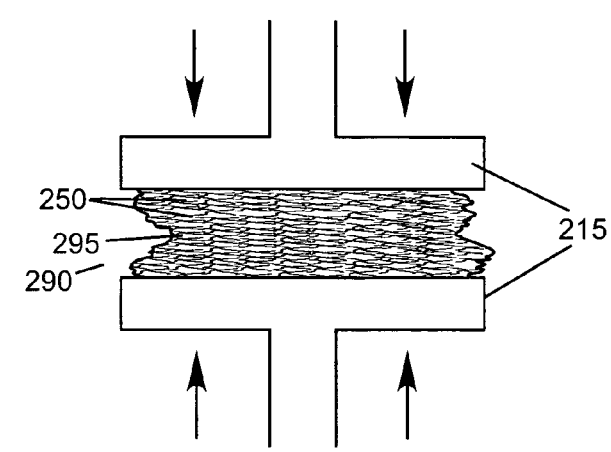

In another embodiment depicted in FIG. 2A, the fibrous matrix material 200 is placed between two compressive devices 210 (e.g., platens, pistons, etc.), which may or may not be heated or cooled. Heating can be used for such purposes as to modify the fibers (e.g., -denature, soften, melt), increase the rate of fluid evaporation, fuse the fibers once compressed, or improve the activity of any lubricant. Cooling can be used for such purposes as protecting the fibers from excessive heat during compression or to induce phase change or thickening of the suspension fluid and/or lubricant. The fibers 220 and the inter fiber void space 230 define the structure of the fibrous matrix material. In FIG. 2B, the top compressive device 215 is lowered to compress the fibrous matrix material 240 while the compressive device 210 remains stationary. A gradient is formed starting at the top of the material where fibers 250 are forced together, reducing the interfiber void space 230, while the fibers 220 in the lower part of the material retain their conformation. This can be employed to create an implant for biphasic tissues such as bone or cartilage. Two gradients can be formed by compressing the fibrous matrix material 260 with both compressive devices 215 at the same time, as shown in FIG. 2C. The top and bottom surfaces have a majority of compressed fibers 250. The next top and bottom layer of fibers 280 will be mildly compressed and have a reduced inter fiber void space 270. The middle of the material 260 will have fibers 220 that maintain their original inter fiber void space 230. This can be employed to create an implant for a triphasic tissue such as the skull that transitions from cortical bone to cancellous bone and back to cortical bone. As shown in FIG. 2D, if compressive devices 215 continue to exert force the material 290 could be evenly compressed with no gradients. The compressed fibers 250 and inter fiber void space 295 will be evenly distributed, or nearly so, through the material 290. Continued compression by compressive devices 215, as shown in FIG. 2E initiates migration of fully compressed fibers 296 in the material 297. This further reduces the inter fiber void space 298. This is useful in the creation of sheet implants having superior strength and finely controlled porosity to replace those currently manufactured for such applications as dura, tendon and hernia repair.

It is envisioned that desired percentages of porosity or desired pore distribution can be controlled based on the amount and method of compression. Specific pore volumes or densities may promote different types of tissue ingrowth (e.g., bone or vascular tissue ingrowth). Based on desired porosity or density, the fibrous matrix material may act as a cellular scaffold for various uses in tissue engineering.

In another embodiment as illustrated in FIG. 3A, an amorphous mass of fibrous dough 300 containing fibers 310 and inter fiber void space 320 is compressed to form an anisotropic sheet material 330 shown in FIG. 3B. The fibers 340 begin to align in the radial direction as force 350 induces migration of the fibers 340 collapsing the inter fiber void space 360.

Figure 4:
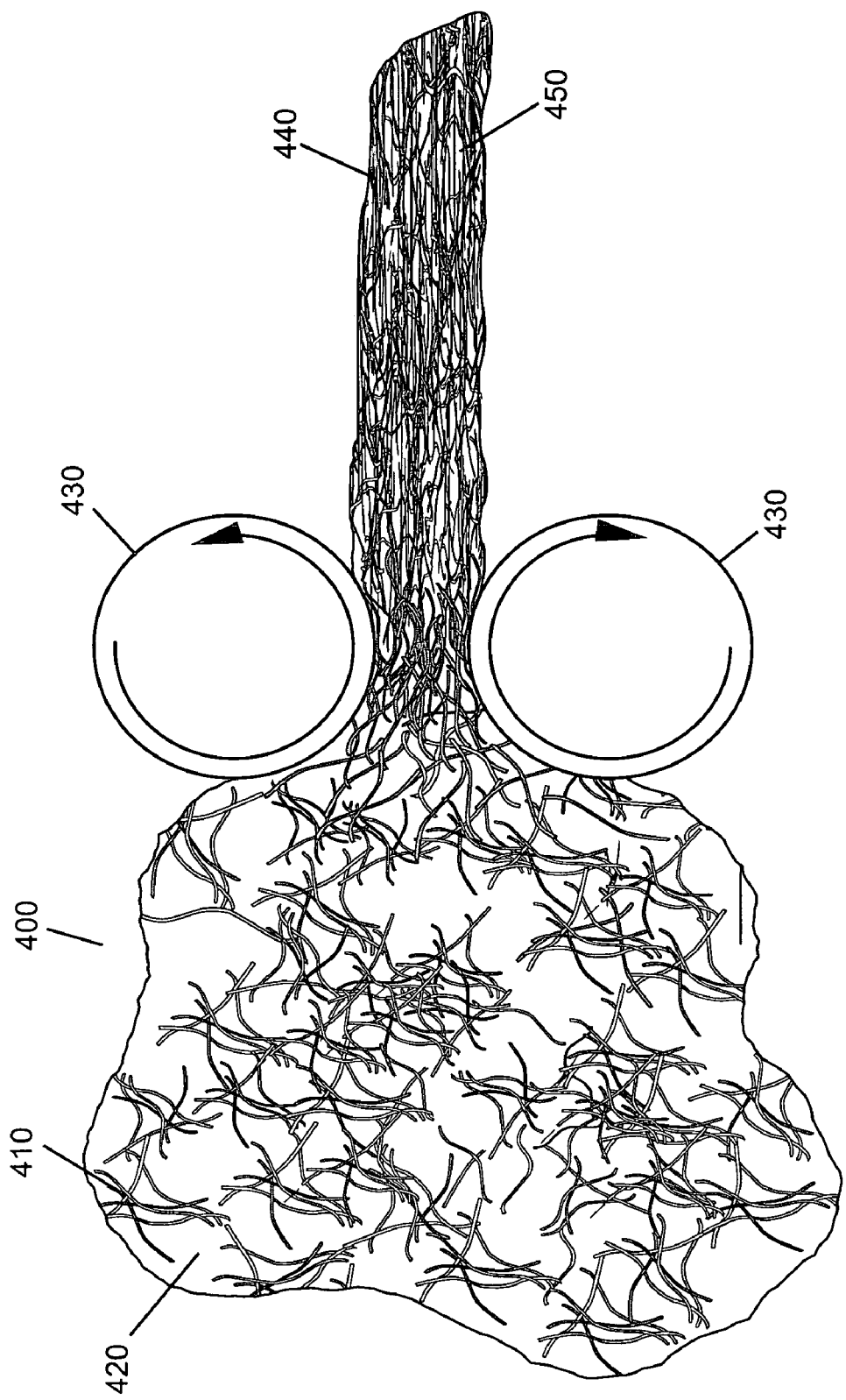
FIG. 4 depicts compression of fibrous dough as it passes through rollers.

Another form of compression is illustrated in FIG. 4. An amorphous mass 400 containing fibers 410 and inter fiber void space 420 is drawn through rollers 430. This drawing motion compresses and aligns fibers 440 while simultaneously reducing the inter fiber void space 450. The rollers could also be aligned circumferentially around the mass and used to draw the material into an elongated cylinder (not shown).

Another form of compression utilizes centrifugal force to compress fibers in an outward direction onto a porous structure. For example, the fibers could be forced out against a spinning porous drum creating a cylinder of compressed fibrous material (not shown). The drum could contain any number of contours or structures that would form corresponding negatives and positives in the fibrous material. Such a method could be used to create detailed anatomical structures such as the cheek, nose or ear. Additionally, this process could be used to create multi-layered constructs or embed materials such as sutures, particulates or meshes into the fibrous constructs. In another preferred embodiment, the above formed multi-layer construct is placed over a mandrel and further compressed creating a structure useful for tissue engineering applications such as vascular grafts, where each layer corresponds to the individual layers within an artery. In another embodiment, the above mandrel is replaced by a series of fibers or threads, which may or may not be woven or spun together, wherein the compressed fibrous material interpenetrates/interdigitates the series of fibers or threads, locking them into a conformation suitable for tendon, ligament or muscle repair.

In another embodiment as illustrated in FIG. 5, a sphere 500 of fibrous matrix material is three-dimensionally compressed by force 510. Fibers 520 separated by inter fiber void space 530 create the sphere's 500 structure. After being compressed, the porosity, inter fiber void space and size of the sphere 540 are decreased. Unlike two-dimensional compression, the fibers 550 have not collapsed into thin layers. The three-dimensional compression caused each fiber 550 to fold or coil as the inter void space 560 was reduced. This embodiment could be used as a device to promote staged delivery of biologically active agents or it could be split in half to create a chin or cheek implant, for example. A polymeric material could be placed in the center to release a biologically active agent (not shown). This embodiment may also be used to create a cell based implant wherein the cells supported in the non-compressed center of the device are protected from the body's immune system by the collapsed porous exterior. The center could also be hollowed out by using a central core material (e.g., ice, polymer, salt, etc) that could function similar to a porosifying agent and be removed after compression and replaced with cells (not shown). This would be particularly useful in supporting and protecting transplanted tissue (autograft or xenograft) such as islet cells capable of producing insulin. While the compressed fibers 550 would prevent immune cells from entering the sphere 540 and destroying the islet cells, oxygen and nutrients would readily pass through the compressed inter fiber space 560. In turn, waste product and insulin would pass out of the sphere.

A modified three-dimensional compression is illustrated on a cylinder 600 of fibrous matrix material in FIG. 6. Like the sphere 500, the cylinder 600 is composed of fibers 610 separated by inter fiber void space 620. Compression can be applied to the cylinder 600 by applying force around the circumference of the cylinder 600 while restricting elongation (or increasing) of its height. This type of three-dimensional compression would cause the compressed cylinder's 630 fibers 640 to pack together as the inter fiber space 650 is reduced. If elongation is encouraged, the fibers would draw out as the inter fiber space is reduced (not shown). Depending on the amount of compression, and direction of fiber migration, the fibers 640 could define thin channels running parallel to each other throughout the height or width of the cylinder 630. Devices like this would be useful as orthopedic rods or nerve guides. Placement of one or more removable solid rods in the center of the mass would allow for the formation of one or more lumen within the cylinder. Uses would include tissue engineering of vessel and nerves as well as any other tubular tissue.

Figure 7A:
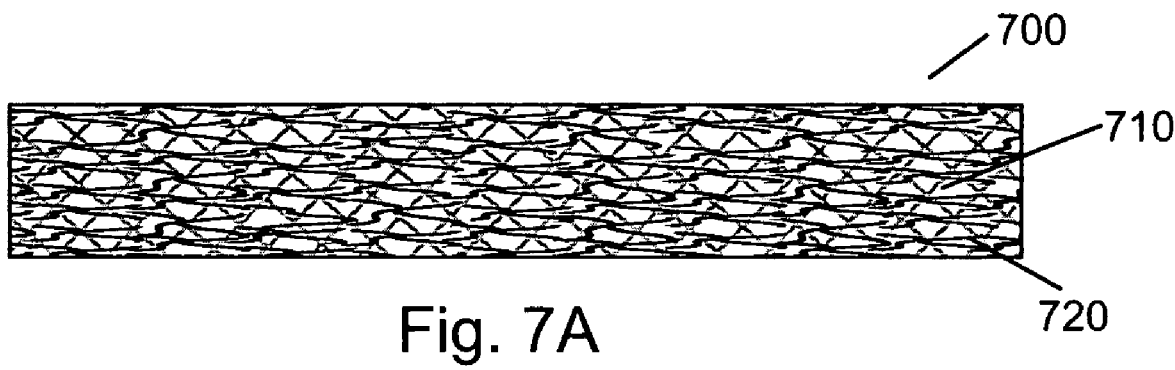
FIG. 7 depicts incorporation if reinforcing materials within compressed fibers.

In another embodiment, the compressed fibrous material contains reinforcing materials such as long threads, meshes, rods, and other fibers. The migration of the fibers under the compressive force may confine, and lock the reinforcing material within a spatial conformation. This could retard the reinforcing material from migrating within, or dissecting from, the compressed fibrous material. This phenomenon can be used to alter mechanical properties (e.g., tear strength) of the construct. Additionally, the compressed fibrous material may improve the biocompatibility of the reinforcing material (e.g., improved cellular migration within or adhesion to a mesh). FIG. 7A shows a construct 700 comprised of an embedded mesh/screen 710 embedded/entangled within the fibers 720.

Figure 7B:
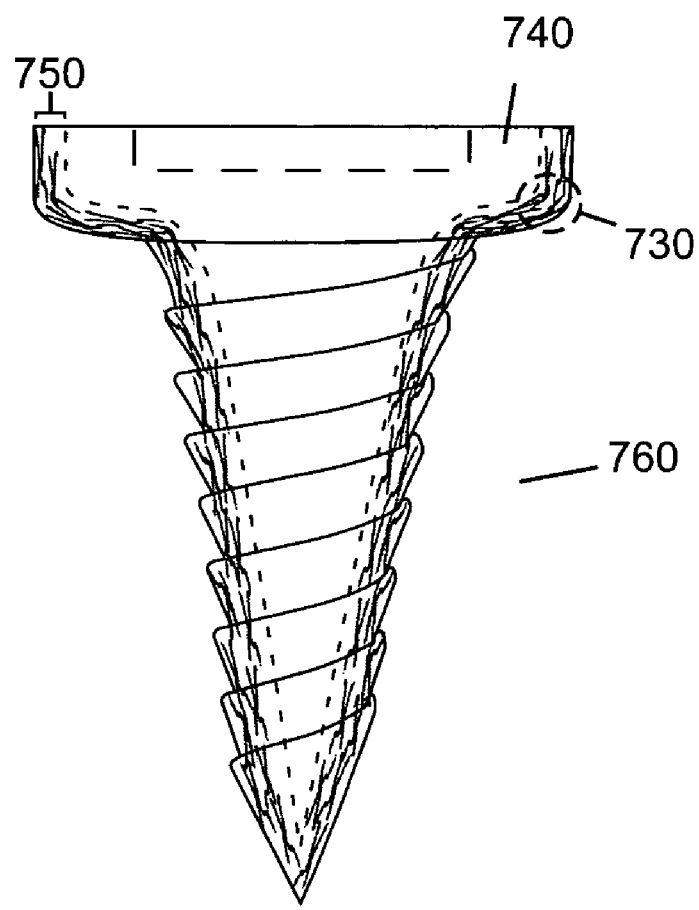

The reinforcing material may be centered within the construct, located on or just below one or more surfaces or interspersed throughout the entire construct. As an example shown in FIG. 7B, the fibrous material 730 may be compressed over a bone screw 740 creating a coating 750 approximating the shape of the screw that is used to temporarily or permanently hide the material of the screw from the body's immune system. The coated implant 760 is useful as an improved interference screw. Additionally, the reinforcing material may be porous and permit interdigitation of the fibers. This porosity also assists in the removal of fluid/lubricant during compression. If desired, vacuum can be used to facilitate drawing of fluid and fibers into the porosity. The lubricant may itself function as a bridging agent locking the fibrous coating to the porous reinforcing material.

Figure 8:
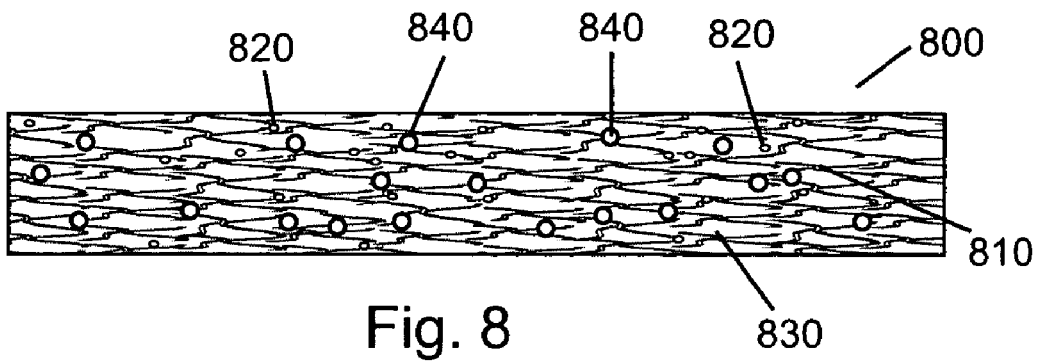
FIG. 8 depicts incorporation of particulates, biologics within the compressed fibrous matrix.

In another embodiment, as seen in FIG. 8, a device 800 containing compressed fibers 810 are used to control the location and delivery of biologically active agents 820 (e.g., growth factors, cytokines, genes, hormones, BMP, drugs, cells, viruses, etc., see Table 2). The unique compressive forces used to create the device can be used to control flow of fluid (e.g., blood, interstitial fluid, etc.) within the device during processing, allowing for tailored release properties. The biologically active agents 820 could be located within or supported between the compressed fibers 810 making up the device 800. Additionally, the biologically active agents 820 could be physically or chemically attached or bonded to the fibers 810 or suspended within a hydration fluid that is supported within the inter fiber void space 830. This hydration fluid may contain a soluble polymer that suspends or binds the biologically active agent. Additionally, the hydration fluid containing the soluble polymer may be removed leaving the soluble polymer as a coating on the compressed fibers or microstructure suspended within the inter fiber void space between the compressed fibers.

In another embodiment, also shown in FIG. 8, the compressed fibers 810 are used to control the location and orientation of reinforcing and/or biologically active particulate components 840 compounded into the fiberous material (e.g., tricalcium phosphate, hydroxyapatite, calcium sulfate, autologous bone graft, allograft bone matrix, DBM, polymers, microspheres, etc; additionally, see Table 3). The compressed fibers 810 may confine, and lock the particulate components 840 within the inter fiber void space 830. This retards the particulate from migrating within or disassociating from the compressed fibrous device/construct 800. When adding particulate, the addition of a lubricant facilitates movement of the particulate within the construct during the compression step preventing stratification or clumping of the particulate in the final product. Additionally, the lubricant can be left within the polymer as a velour or coating entrapping the particulate.

It should also be noted that the use of reinforcing materials (e.g., polymer mesh, titanium screens, TCP, etc.) or addition of biologically active agents (e,g, growth factors, DBM, cells, drugs, etc.) may be employed as or in a fiber, rod, thread, wire, particulate, microsphere, fragment, suspension, emulsion or other addition. These materials can be uniformly distributed throughout the compressed fibrous construct, or if desired, stratified or concentrated to specific areas of the construct. This can be easily achieved by placing depots of materials between two or more layers of fibrous material prior to compression, as well as by the methods previously discussed.

Figure 9A:
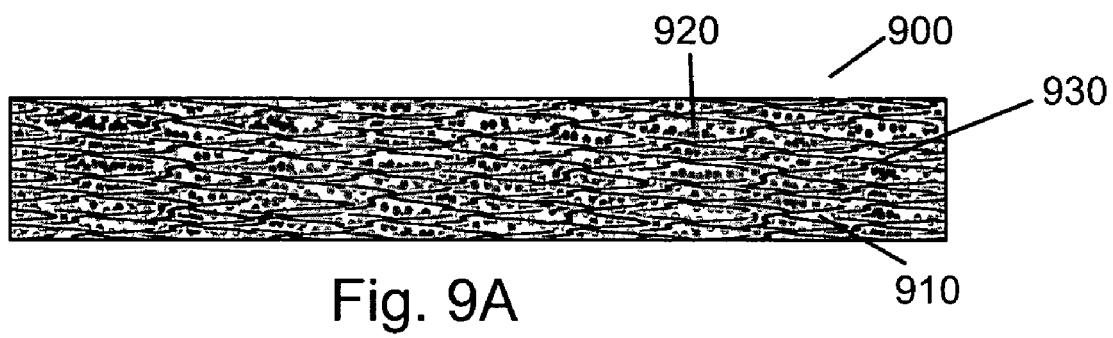
FIG. 9 depicts incorporation of microstructures within the compressed fibrous matrix.
Figure 9B:
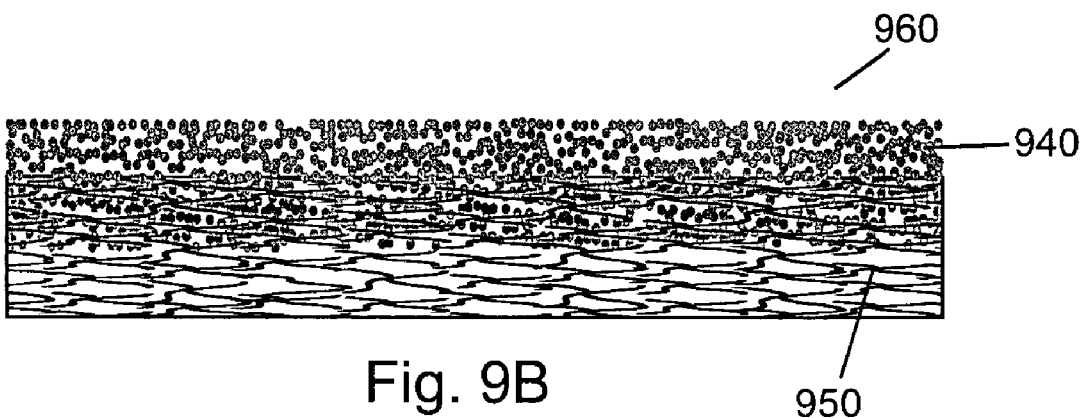

It is also conceived that in one embodiment of this invention the material can contain an additive that can be used to help deliver or retain the previously described biologically active agents. As an example shown in FIG. 9, the inter fiber void space 910 of the gross compressed fibrous structure 900 could be invested with a chemotactic ground substance 920, such as the velour of hyaluronic acid suspended between the compressed fibers 930. A velour could accomplish several biochemical and biomechanical functions essential for wound repair. For example, since hyaluronic acid is extremely hydrophilic, it may be valuable for drawing body fluid (e.g., blood, bone marrow) or other fluid-based biologically active agents into the fibrous device. Upon hydration, the hyaluronic acid can become an ideal carrier for pharmacological or biologically active agents (e.g,. osteoinductive or osteogenic agents such as the bone morphogenetic protein (BMP) and other bone-derived growth factors (BDGF)) by providing for chemical binding sites, as well as by providing for mechanical entrapment of the agent as the velour forms a hydrogel. It is further conceived and shown in FIG. 9B that the velour 940 extend beyond the boundaries of the compressed fibers 950, creating a layer of microstructure attached to the compressed fibrous structure. This bi-phasic device 960 is useful as an adhesive bandage when the microstructure is a tissue adhesive agent.

In another embodiment, the material may be cross-linked to impart improved characteristics such as: mechanical strength (e.g., suturablity, compression, tension, etc.), and biodurability (e.g., resistant to enzymatic and hydrolytic degradation). This may be accomplished using several different cross-linking agents, or techniques known to those skilled in the art (e.g., thermal dehydration, radiation, EDC, aldehydes (e.g., formaldehyde, glutaraldehyde, etc.), natural agents such as genipin or proanthocyanidin, and combinations thereof).

In another embodiment, a sheet produced by methods previous described may be rolled, contoured or shaped prior to cross-linking to lock the sheet into a unique spatial configuration, for example, a spiral configuration may be created having a plane separating each successive revolution of the sheet. The plane provides unique compressive qualities, that when combined with the compressive qualities of the cross-linked compressed fibers, is ideal for applications receiving directional compressive loads. These applications include but are not limited to joint meniscus, intervertebral disk and articular cartilage. In another embodiment, the plane formed by the spiral configuration can be filled with materials to enhance its mechanical or biologic characteristics (e.g., reinforcing materials, particulates, biologically active agents, natural and synthetic polymers).

Figure 10:
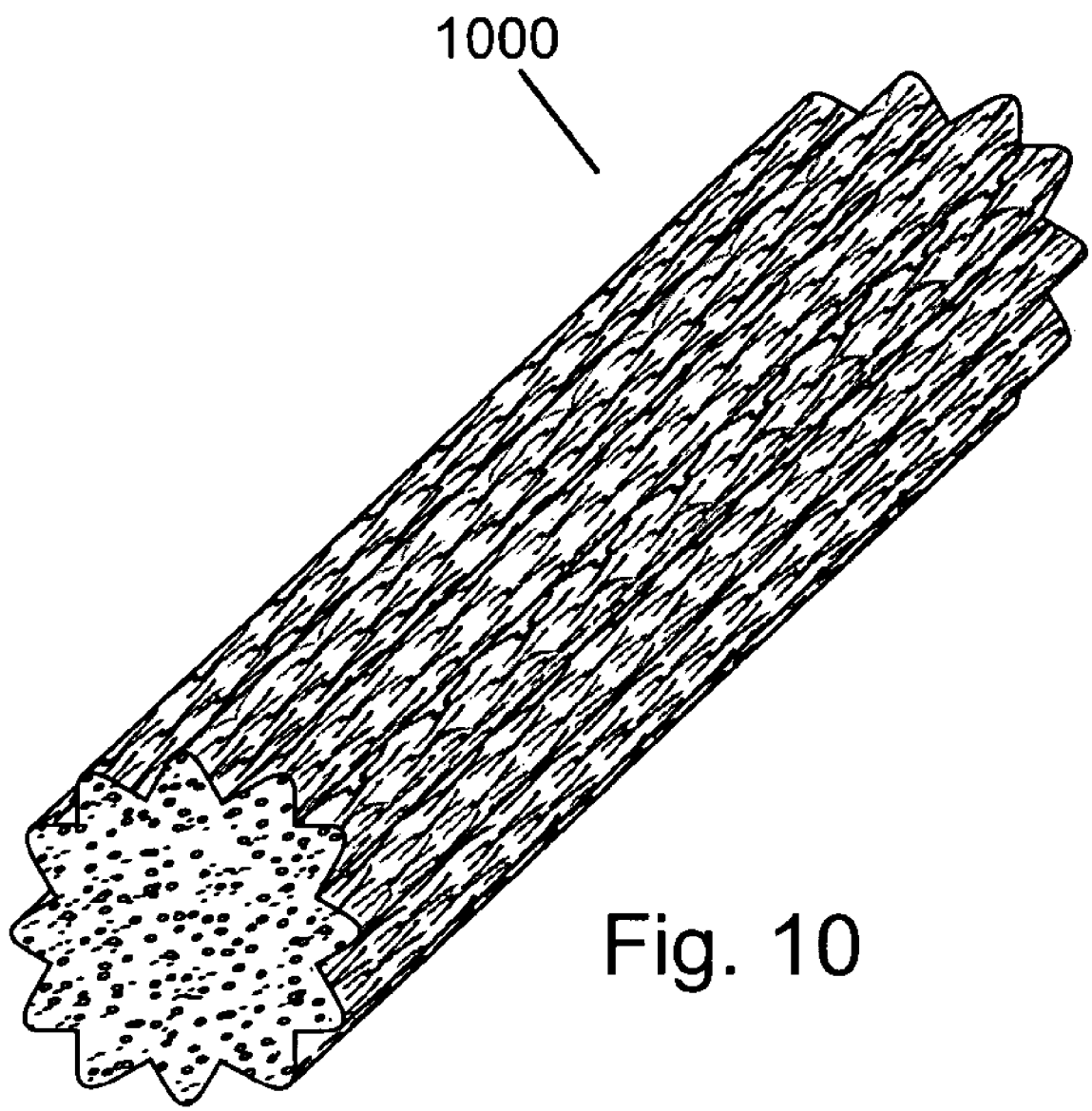
FIG. 10 depicts a hemostatic tract plug of compressed fibrous matrix.

In another embodiment, fibers can be compressed directly into a mold that approximates the gross anatomy of a tissue or organ (e.g., blood vessel, heart valve, ear, nose, breast, fingerbones, etc.) after which the construct may be cross-linked. The reduced inter fiber void space of the compressed fiber provides superior shape holding characteristics due to the unique resistance to fiber disassociation. A star-shaped structure 1000 shown in FIG. 10 illustrates a possible design for a hemostatic tract plug made possible by the superior shape-holding characteristics of the present invention. Preferably such a device is not cross-linked to provide the shortest resorption time post implantation. Upon exposure to body fluids the construct swells, creating a tampanode effect. Due to the compressive forces used during fabrication, the fibers do not readily disassociate from the unit. If cross-linking is desired, it is preferable to cross-link the outer surface only so that the interior fibers are able to swell. As the center of the device swells, the star's concave portions are pushed out creating a cylinder that seals the wound site.

Such a swellable device has applications which include the occluding of other openings, ducts or lumens in the body (both natural and artificial) and that it can be utilized to deliver biologically active agents and drugs. Additionally, those skilled in the art will recognize other useful shapes (e.g., threaded, oval, square, circle, etc.) for specific applications (e.g., bone plug, plastic or cosmetic surgery, oviducts, etc.). Such constructs can be delivered through cannulas or by syringe-like devices.

Figure 11A:
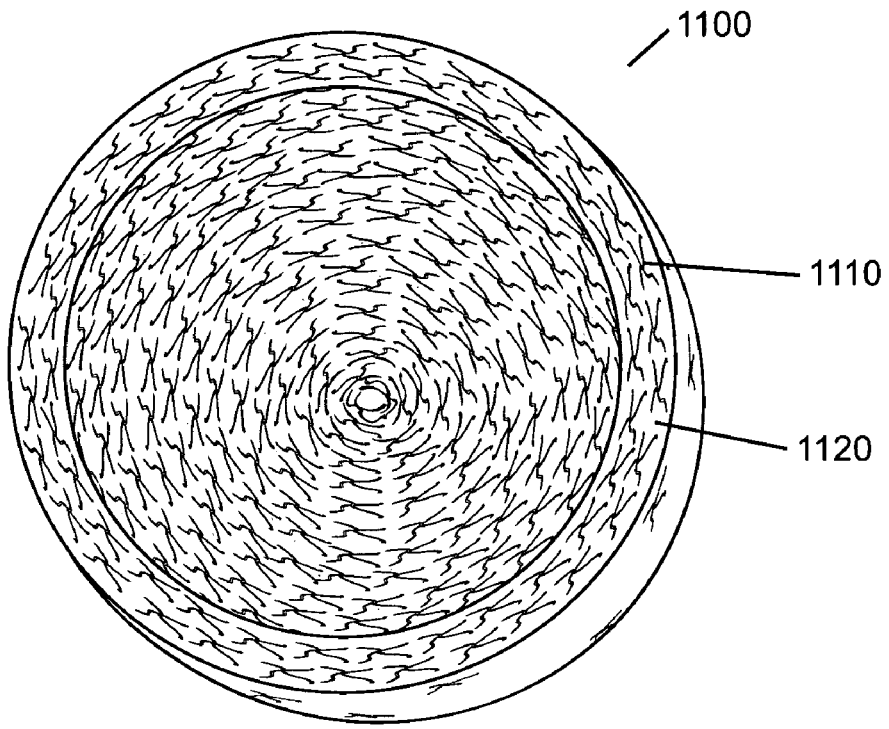
FIG. 11 depicts hemispherical cups of compressed fibrous matrix.
Figure 11B:
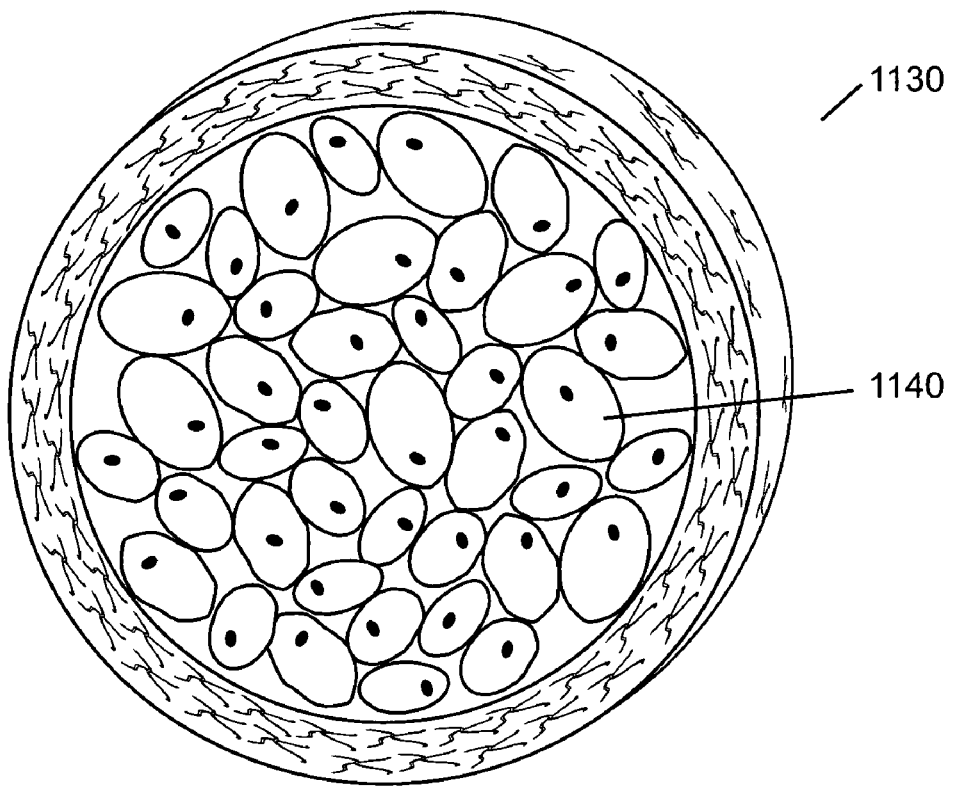

In another embodiment, shown in FIG. 11A, a hollow hemi-spherical device 1100 depicts circumferentially aligned and compressed fibers 1110 and corresponding inter fiber void space 1120. Methods of producing said construct include compressing masses of fibrous dough-like material around spherical and hemi-spherical molds with and without rotation of the compression device and formation of bladders as previously described. FIG. 11B illustrates a cross section of a hollow device 1130 that contains a material 1140. This material 1140 (e.g., cells, particulate, gel or fluid-like material, settable materials, etc.) may have been placed in the hollow device prior to or after implantation. Hollow structures as described above are useful for tissue engineering applications such as in-vivo cell reservoirs, drug delivery systems, plastic and reconstructive surgery implants, and shock absorbing indications as previously described. For example, bladders could be formed to receive autologous fat cells, which could be relocated within the body for cosmetic augmentation.

In another embodiment, a bladder manufactured by above methods may be used to reduce and repair a fractured vertebral body by inserting the bladder into the injury site and inflating (e.g., gel or fluid, settable fluid, etc.) to realign the spinal column by returning the vertebra superior and inferior of the injury site to their appropriate location.

Figures 12A, 12B:
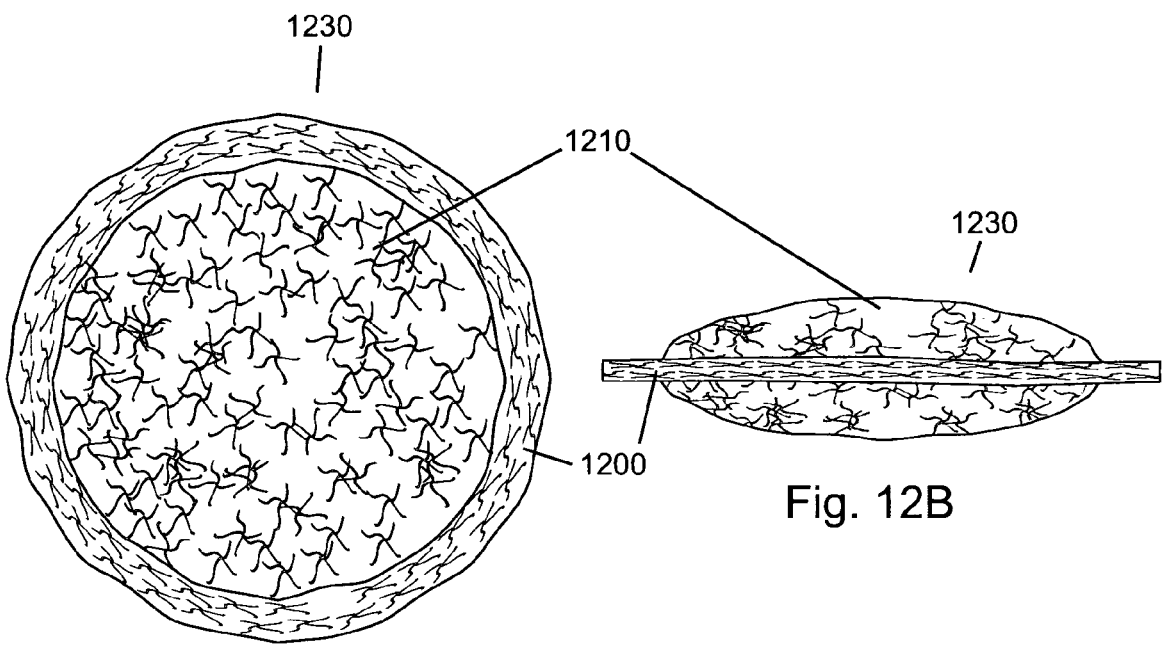
FIG. 12 depicts a selectively compressed ring of fibrous matrix surrounding a non-compressed fibrous matrix.
Figure 13:
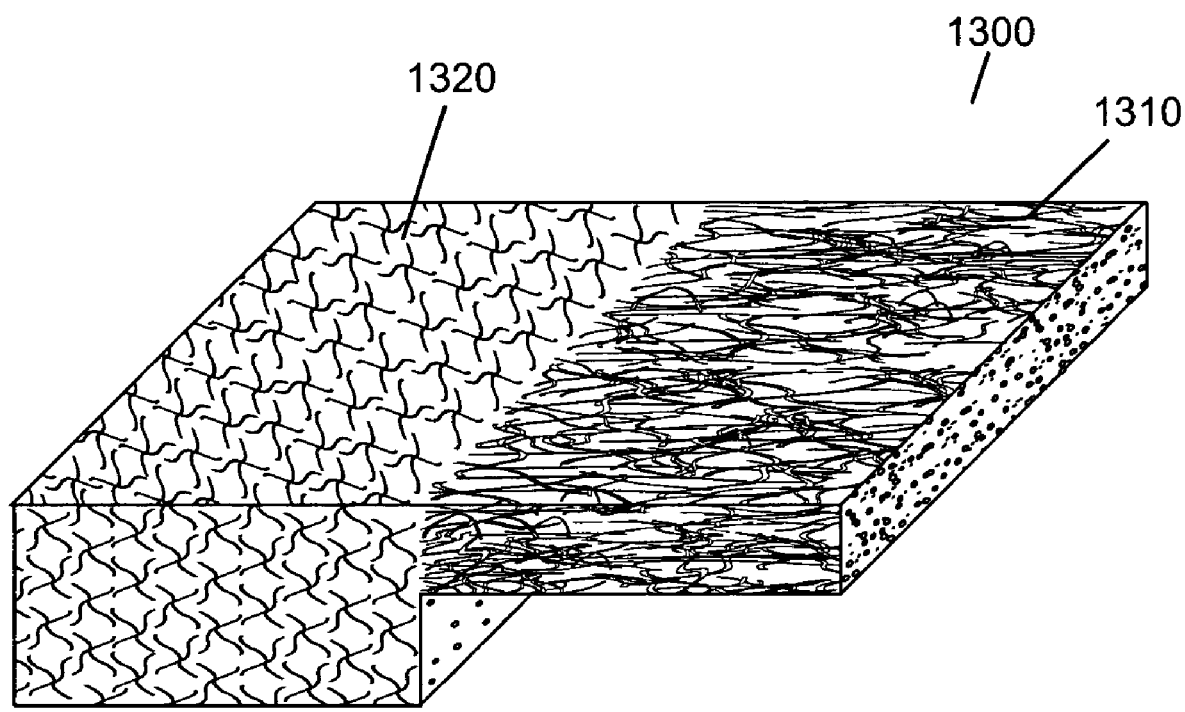
FIG. 13 depicts selective compression of a fibrous matrix.

In another embodiment, shown in FIG. 12A (top view) and FIG. 12B (side view), a ring of material 1200 is selectively compressed surrounding a minimally-compressed to non-compressed fibrous region 1210. The device 1230 is useful in such applications such as a hernia patch or where a sponge-like material is needed with the additional requirement of suturability around the periphery of the device. Similar to FIGS. 12A and 12B, FIG. 13 depicts a device 1300 that contains a preferentially compressed region 1310 adjacent to a minimally-compressed to non-compressed region 1320. Such a device may be useful in the repair of transitional zones between tissues such as tendon to muscle or ligament to bone.

It is believed that the high compressive forces will create chemical linkages aside from the physical interaction of the fibers. In the case of collagen, it is believed that the compressive force re-establishes non-covalent forces such as hydrogen bonding, hydrophobic/hydrophilic interactions, and electrostatic interactions, that the individual fibers and fibrils previously embodied in the native, pre-extracted tissues. These additional chemical linkages may act to create a pseudo-molecular weight increase to the matrix, providing improved mechanical properties prior to cross-linking, thereby providing for highly detailed crisp margins within the compressed fibrous construct that are locked in place with cross-linking. Constructs made using fibrous materials defined in the prior art do not hold crisp margins. Therefore, material in this embodiment would be useful as, but not limited to, devices for cosmetic and reconstructive surgery, intervertebral disks, joint meniscus and hollow tissues and organs (e.g., intestine, esophagus, ureter, etc.).

In another embodiment, a fibrous material can be compressed into a mold containing a structure or component (e.g., ring, mesh, particulate, screw, rod, etc.) to which the fibers attach, after which cross-linking may occur. The compressed fibers support, confine, and lock the structure or component within a spatial conformation. Additionally, the structure or construct may be porous and permit interdigitation of the fibers. This porosity also assists in the removal of fluid/lubricant during compression. If desired, vacuum can be used to facilitate drawing of fluid and fibers into the porosity. The lubricant may itself function as a bridging agent locking the fibrous coating to the porous reinforcing material.

Additionally, the compressed fibrous material may contain reinforcing materials such as long polymer threads or mesh (es) or may include particulates or biologically active agents. (e.g., growth factors, hormones, bmp, drugs, cells, viruses, etc.) Additionally, the biologically active agents could be located within fibers making up the compressed fibrous material, mechanically or chemically attached to the fibers making up the compressed material, between the fibers in the inter fiber void space, or suspended within a hydration fluid or second soluble polymer suspended in the inter fiber void space. The biologically active agents and/or soluble polymer may be added prior to or after fiber compression and prior to or after cross-linking.

In various embodiments, the fibrous matrix material may be composed of layers of the same or different types of polymers. It is envisioned that this invention may be useful for medical devices that require specific abilities, material or mechanical properties, or biological conditions to function optimally in the body. For example, devices may undergo changes in loading over time, require specific degradation rates, may be loaded differently across the surface of the implant, etc. To accommodate the special requirements of some devices, layers of different compressed fibrous matrix material may be layered with two or more different polymers comprising one device. The layers of compressed fibrous material may increase or decrease degradation, provide controlled drug delivery to specific locations, etc. The layers may be stacked on one another or side-by-side. The layers may be fused together and may be separated by layers of biologics, particulates, or reinforcing materials. The layers will provide the device the ability to be multi-functional. For example, one or more layers will perform one function (e.g., provide structurally integrity, maintain shape, etc.) for the device while one or more other layers perform another function (e.g., drug delivery, allow tissue ingrowth). Another way to modify the device is by compressing the layers by different methods or by different amounts of compression.

In another embodiment, two or more pre-compressed fibrous masses of dough-like material may be layered and compressed to create a laminated structure. The fibrous mass may or may not consist of different polymers. Depending on the starting material composition and compressive forces used, resultant constructs range in composition from a single homogeneous structure to a multi-layered laminate. Gradients and/or laminates may also be created in a similar fashion by layering multiple sheets of varying compressions and composition before applying a final compression to laminate them into a single unit. In another embodiment, reinforcing materials, foamed polymer sheets, biologically active agents, sheets of microstructure, particulates, etc. may be placed between the layers before compression. In another embodiment, a pre-compressed sheet is roll-compressed, radially creating a spiral laminate suitable for controlled drug delivery and creation of nerve guides when wrapped around a removable central core material.

Figure 14A:
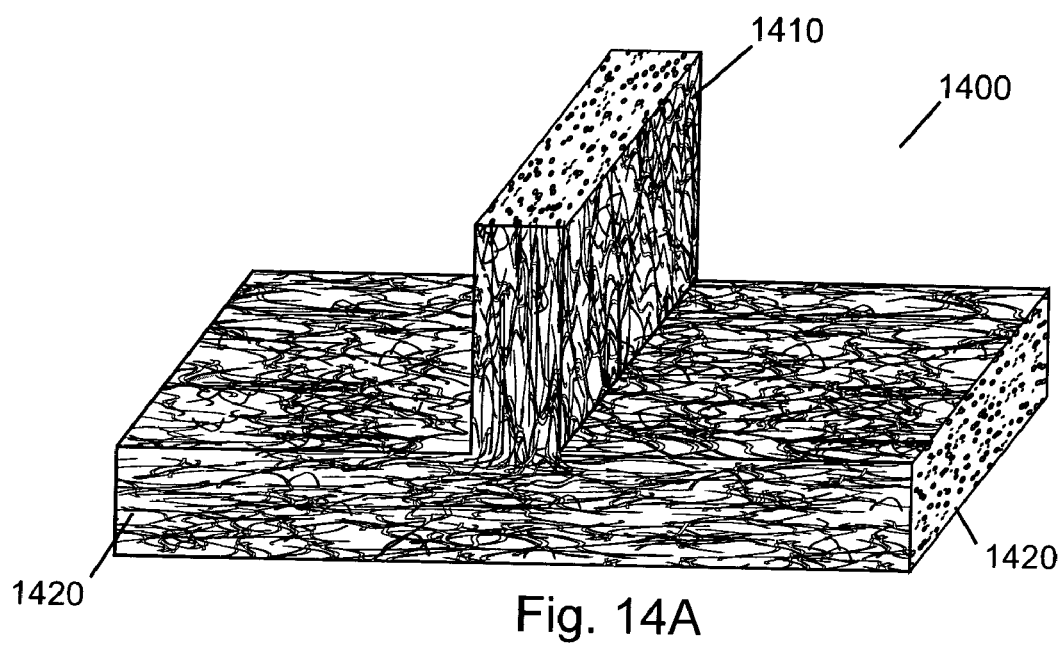
FIG. 14 depicts compressed fibrous constructs useful surgical applications.
Figure 14B:
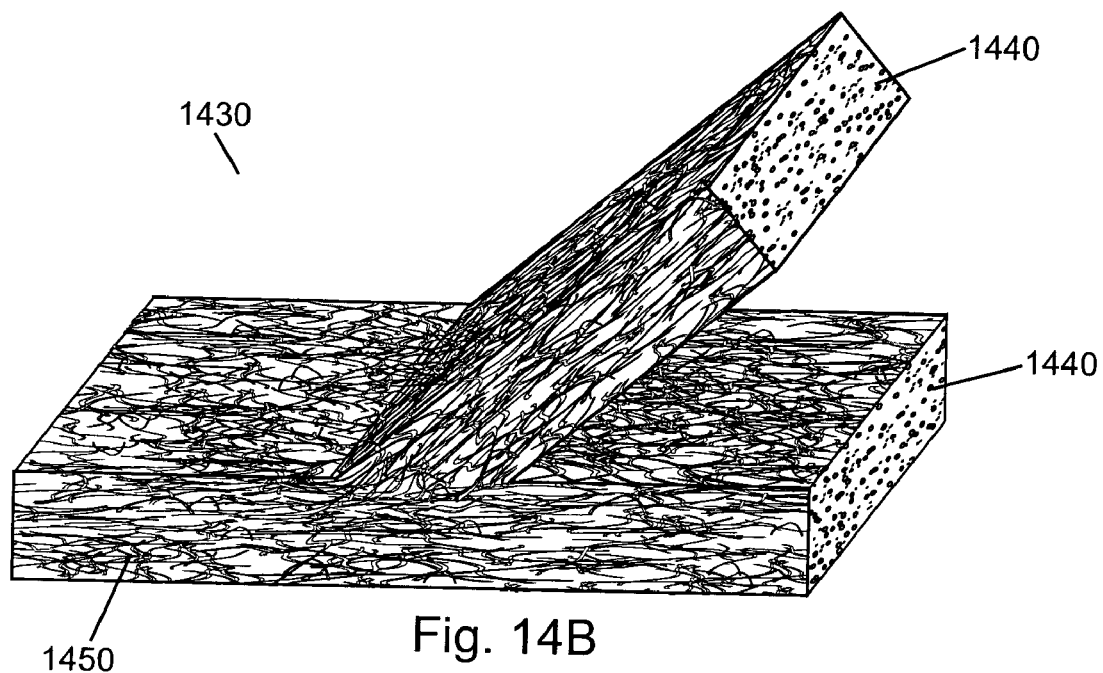

In another embodiment, compressed porous matrix material can be machined or molded into distinctive geometric shapes useful as internal fixation devices used for surgical repair, replacement, or reconstruction of damaged bone or soft tissue in any area of the body. Internal repair devices may be successfully employed for many conditions, such as orthopedic, spinal, maxiofacial, craniofacial, etc. Compressed fibrous matrix material can be machined or molded into any configuration. In various embodiments illustrated in FIGS. 14A and 14B, internal fixation, trauma, or sport medicine devices may be fabricated into any configuration from the compressed fibrous matrix material. For example, the device 1400 shown in FIG. 14A is a T-shaped compressed fibrous construct intended for implantation into an osteoarthritic joint. Tab 1410 separates the damaged joint surfaces and functions as a cushion while wings 1420 provide anchorage points to prevent migration of the device. Device 1430 shown in FIG. 14B is a Y-shaped compressed fibrous construct intended for repair and reinforcement of damaged ligaments and tendons. In a ligament application/procedure the damaged tissue is placed in between tabs 1440 and secured in place with tacks, staples or sutures. Extension 1450 is then approximated to the original insertion point on the long bone and secured by methods such as interference screws, tacks or staples. Additional applications, such as an augmentation device for the anterior cruciate ligament (ACL), for constructs illustrated in FIGS. 14A and 14B or similar constructs will be obvious to those skilled in the art.

Figure 15:
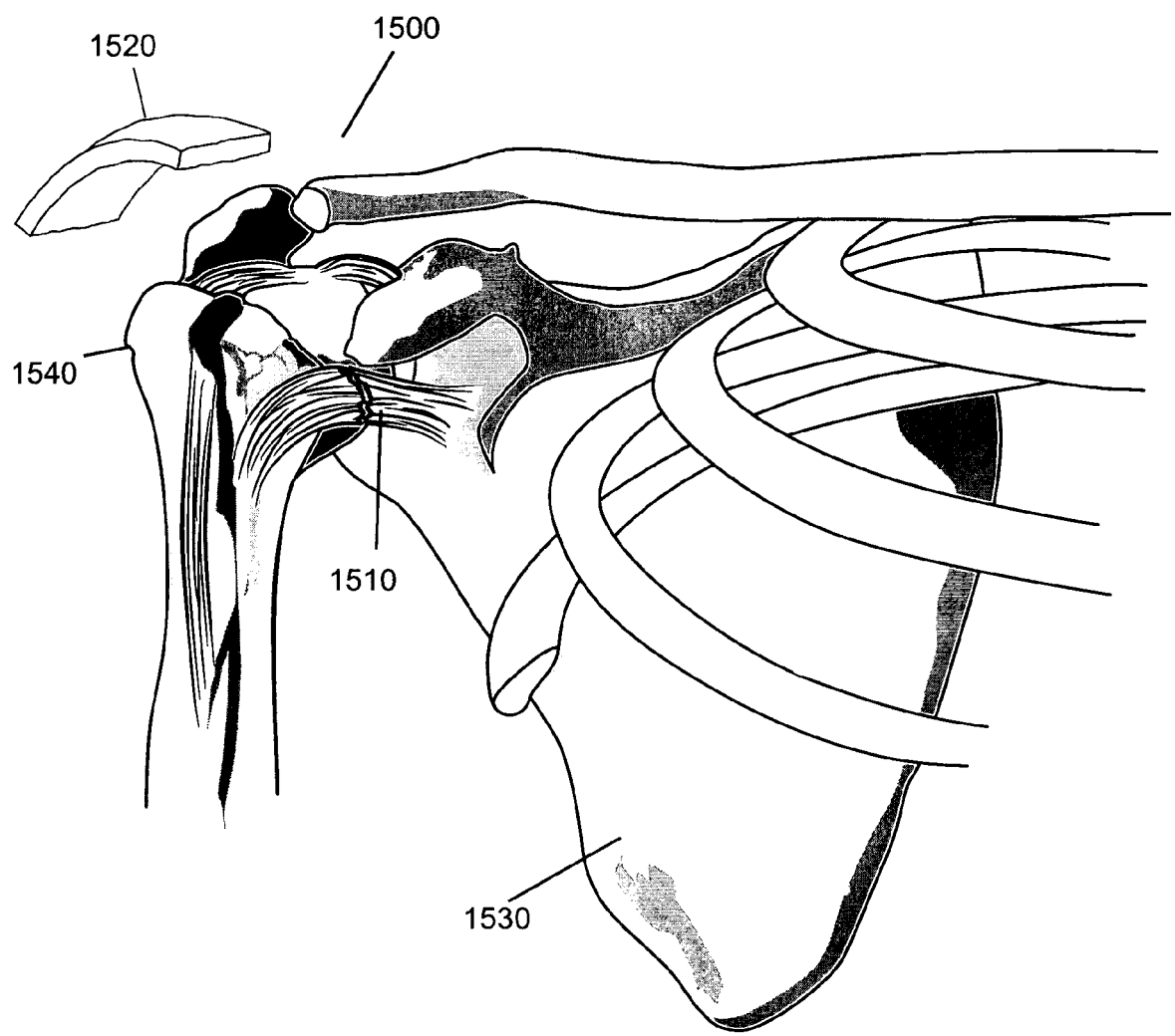
FIG. 15 depicts the surgical application of a compressed fibrous construct.

One embodiment of the device can be used to aid in the repair of muscle and tendon surrounding a joint. In FIG. 15, a glenohumeral joint 1500 in which damaged tissue 1510 encompassing the rotator cuff is shown along with the device 1520. The rotator cuff is made up of the confluent tendons of four muscles (i.e. supraspinatus, infraspinatus, subscapularis, teres minor) originating on the scapula 1530, and is also associated with tendon from the long end of the bicep. These muscles control the proximal end of the humerus 1540, which is inserted into the glenoid cavity of the scapula. The damage to the rotator cuff may be a tear in one of the tendon insertions (for example a crescent or an acute L-shaped tear of the supraspinatus). In this case, the invention can be used as a reinforcement patch. The tear is repaired by normal suturing, and is then protected and reinforced by overlaying the repair with the invention. The muscle will be able to function, but while it is healing, the reinforcement patch takes on some of the load. Additionally, tissue will become integrated within the pores of the overlay graft and the implant will add bulk mass and strength to the repaired muscle tissue. In the situation where the torn muscle and tendon cannot be fixed by suture alone, an alternate use for the invention is to act as an artificial tendon. In the example of a torn infraspinatus tendon, the invention is sutured to a secure area of the torn infraspinatus. The implant material can then bridge the necessary distance and be sutured to the posterior aspect of the greater tuberosity of the humerus.

TABLE 1

Examples of Biodegradable Polymers for Construction of the Fibrous Device

Aliphatic polyesters
Cellulose
Chitin
Collagen
Copolymers of glycolide
Copolymers of lactide
Elastin
Fibrin
Glycolide/l-lactide copolymers (PGA/PLLA)
Glycolide/trimethylene carbonate copolymers (PGA/TMC)
Hydrogel
Lactide/tetramethylglycolide copolymers
Lactide/trimethylene carbonate copolymers
Lactide/ε-caprolactone copolymers
Lactide/σ-valerolactone copolymers
L-lactide/dl-lactide copolymers
Methyl methacrylate-N-vinyl pyrrolidone copolymers
Modified proteins
Nylon-2
PHBA/γ-hydroxyvalerate copolymers (PHBA/HVA)
PLA/polyethylene oxide copolymers
PLA-polyethylene oxide (PELA)
Poly (amino acids)
Poly (trimethylene carbonates)
Poly hydroxyalkanoate polymers (PHA)
Poly(alklyene oxalates)
Poly(butylene diglycolate)
Poly(hydroxy butyrate) (PHB)
Poly(n-vinyl pyrrolidone)

TABLE 1-continued

Examples of Biodegradable Polymers for Construction of the Fibrous Device

Poly(ortho esters)
Polyalkyl-2-cyanoacrylates
Polyanhydrides
Polycyanoacrylates
Polydepsipeptides
Polydihydropyrans
Poly-dl-lactide (PDLLA)
Polyesteramides
Polyesters of oxalic acid
Polyglycolide (PGA)
Polyiminocarbonates
Polylactides (PLA)
Poly-l-lactide (PLLA)
Polyorthoesters
Poly-p-dioxanone (PDO)
Polypeptides
Polyphosphazenes
Polysaccharides
Polyurethanes (PU)
Polyvinyl alcohol (PVA)
Poly-β- hydroxypropionate (PHPA)
Poly-β-hydroxybutyrate (PBA)
Poly-σ-valerolactone
Poly-β-alkanoic acids
Poly-β-malic acid (PMLA)
Poly-ε-caprolactone (PCL)
Pseudo-Poly(Amino Acids)
Starch
Trimethylene carbonate (TMC)
Tyrosine based polymers

TABLE 2

Examples of Biologically Active Agents Deliverable via the Present Invention

Adenovirus with or without genetic material
Alcohol
Amino Acids
   L-Arginine
Angiogenic agents
Angiotensin Converting Enzyme Inhibitors (ACE inhibitors)
Angiotensin II antagonists
Anti-angiogenic agents
Antiarrhythmics
Anti-bacterial agents
Antibiotics
   Erythromycin
   Penicillin
Anti-coagulants
   Heparin
Anti-growth factors
Anti-inflammatory agents
   Dexamethasone
   Aspirin
   Hydrocortisone
Antioxidants
Anti-platelet agents
   Forskolin
   GP IIb-IIIa inhibitors
      eptifibatide
Anti-proliferation agents
   Rho Kinase Inhibitors
      (+)-trans-4-(1-aminoethyl)-1-(4-pyridylcarbamoyl) cyclohexane
Anti-rejection agents
   Rapamycin
Anti-restenosis agents
   Adenosine $A_{2A}$ receptor agonists
Antisense
Antispasm agents
   Lidocaine
   Nitroglycerin
   Nicarpidine TABLE 2-continued Examples of Biologically Active Agents
Deliverable via the Present Invention Anti-thrombogenic agents
    Argatroban
    Fondaparinux
    Hirudin
    GP IIb/IIIa inhibitors
Anti-viral drugs
Arteriogenesis agents
    acidic fibroblast growth factor (aFGF)
    angiogenin
    angiotropin
    basic fibroblast growth factor (bFGF)
    Bone morphogenic proteins (BMP)
    epidermal growth factor (EGF)
    fibrin
    granulocyte-macrophage colony stimulating factor (GM-CSF)
    hepatocyte growth factor (HGF)
    HIF-1
    insulin growth factor-1 (IGF-1)
    interleukin-8 (IL-8)
    MAC-1
    nicotinamide
    platelet-derived endothelial cell growth factor (PD-ECGF)
    platelet-derived growth factor (PDGF)
    transforming growth factors alpha & beta (TGF-.alpha., TGF-beta.)
    tumor necrosis factor alpha (TNF-.alpha.)
    vascular endothelial growth factor (VEGF)
    vascular permeability factor (VPF)
Bacteria
Beta blocker
Blood clotting factor
Bone morphogenic proteins (BMP)
Calcium channel blockers
Carcinogens
Cells and cellular material
    Adipose cells
    Blood cells
    Bone marrow
    Cells with altered receptors or binding sites
    Endothelial Cells
    Epithelial cells
    Fibroblasts
    Genetically altered cells
    Glycoproteins
    Growth factors
    Lipids
    Liposomes
    Macrophages
    Mesenchymal stem cells
    Progenitor cells
    Reticulocytes
    Skeletal muscle cells
    Smooth muscle cells
    Stem cells
    Vesicles
Chemotherapeutic agents
    Ceramide
    Taxol
    Cisplatin
Cholesterol reducers
Chondroitin
Collagen Inhibitors
Colony stimulating factors
Coumadin
Cytokines prostaglandins
Dentin
Etretinate
Genetic material
Glucosamine
Glycosaminoglycans
GP IIb/IIIa inhibitors
    L-703, 081
Granulocyte-macrophage colony stimulating factor (GM-CSF)
Growth factor antagonists or inhibitors
Growth factors
    Bone morphogenic proteins (BMPs)
    Core binding factor A
    Endothelial Cell Growth Factor (ECGF)
    Epidermal growth factor (EGF)
    Fibroblast Growth Factors (FGF)
    Hepatocyte growth factor (HGF)
    Insulin-like Growth Factors (e.g. IGF-I)
    Nerve growth factor (NGF)
    Platelet Derived Growth Factor (PDGF)
    Recombinant NGF (rhNGF)
    Tissue necrosis factor (TNF)
    Transforming growth factors alpha (TGF-alpha)
    Transforming growth factors beta (TGF-beta)
    Vascular Endothelial Growth Factor (VEGF)
    Vascular permeability factor (UPF)
    Acidic fibroblast growth factor (aFGF)
    Basic fibroblast growth factor (bFGF)
    Epidermal growth factor (EGF)
    Hepatocyte growth factor (HGF)
    Insulin growth factor-1 (IGF-1)
    Platelet-derived endothelial cell growth factor (PD-ECGF)
    Tumor necrosis factor alpha (TNF-.alpha.)
Growth hormones
Heparin sulfate proteoglycan
HMC-CoA reductase inhibitors (statins)
Hormones
    Erythropoietin
Immoxidal
Immunosuppressant agents
Inflammatory mediator
Insulin
Interleukins
Interlukin-8 (IL-8)
Interlukins
Lipid lowering agents
Lipo-proteins
Low-molecular weight heparin
Lymphocites
Lysine
MAC-1
Methylation inhibitors
Morphogens
Nitric oxide (NO)
Nucleotides
Peptides
Polyphenol
PR39
Proteins
Prostaglandins
Proteoglycans
    Perlecan
Radioactive materials
    Iodine - 125
    Iodine - 131
    Iridium - 192
    Palladium 103
Radio-pharmaceuticals
Secondary Messengers
    Ceramide
Somatomedins
Statins
Stem Cells
Steroids
Thrombin
Thrombin inhibitor
Thrombolytics
Ticlid
Tyrosine kinase Inhibitors
    ST638
    AG-17
Vasodilators
    Histamine
    Forskolin
    Nitroglycerin
Vitamins
    E
    C
Yeast
Ziyphi fructus The inclusion of groups and subgroups in Table 2 is exemplary and for convenience only. The grouping does not indicate a preferred use or limitation on use of any drug therein. That is, the groupings are for reference only and not meant to be limiting in any way (e.g., it is recognized that the Taxol formulations are used for chemotherapeutic applications as well as for anti-restenotic coatings). Additionally, the table is not exhaustive, as many other drugs and drug groups are contemplated for use in the current embodiments. There are naturally occurring and synthesized forms of many therapies, both existing and under development, and the table is meant to include both forms.

TABLE 3

Examples of Reinforcing and/or Biologically Active Particulates

Alginate
Bioglass
Calcium Compounds
Calcium Phosphate
Ceramics
Chitosan
Cyanoacrylate
Collagen
Dacron
Demineralized bone
Elastin
Fibrin
Gelatin
Glass
Gold
Hyaluronic acid
Hydrogels
Hydroxy apatite
Hydroxyethyl methacrylate
Hyaluronic Acid
Liposomes
Mesenchymal cells
Nitinol
Osteoblasts
Oxidized regenerated cellulose
Phosphate glasses
Polyethylene glycol
Polyester
Polysaccharides
Polyvinyl alcohol
Platelets, blood cells
Radiopacifiers
Salts
Silicone
Silk
Steel (e.g. Stainless Steel)
Synthetic polymers
Thrombin
Titanium The following examples are given for purposes of illustration to aid in understanding the invention and it is to be understood that the invention is not restricted to the particular conditions, proportion, and methods set forth therein.

EXAMPLE 1

Starting with a dough-like material (90:10 ratio of fibrous collagen (Semed F, supplied by Kensey Nash Corporation) to soluble collagen (Semed S, supplied by Kensey Nash Corporation)) (approximately 20% solids), the composition was rolled into a flat sheet approximately 5 mm thick. This was then sandwiched between two sheets of wicking material, such as a paper towel. This entire arrangement was placed in a 30 ton hydraulic press at 60,000 lbf. The product was left until equilibrium was achieved and no additional water was being expelled from the product at the given pressure. The press was opened and the product was removed as an approximately 1 mm sheet. An expansion of approximately 30-40% was noted in a radial direction. The sheet was cross-linked using 50 mM EDC (pH 5.4) in water. The sheet was soaked overnight in the solution and then serially rinsed 3×for 2 hours with agitation in water. Tear strengths in excess of 120 N were achieved.

EXAMPLE 2

Starting with a fibrous dough-like material (90:10 ratio of fibrous collagen (Semed F, supplied by Kensey Nash Corporation) to soluble collagen (Semed S, supplied by Kensey Nash Corporation)) (approximately 20% solids), the composition was rolled into a flat sheet approximately 5 mm thick. This was then sandwiched between two sheets of wicking material, such as a paper towel. The product was then wrung through a set of high compression rollers allowing the wicking material to remove a large portion of the available water. It was noted the material expanded in both the lengthwise and widthwise directions unless constrained in one direction. The sheet was then freeze dried to preserve the small amount of porosity that was still remaining within the sample.

EXAMPLE 3

Starting with a fibrous dough-like material (85:15 ratio of fibrous collagen (Semed F, supplied by Kensey Nash Corporation) to soluble collagen (Semed S, supplied by Kensey Nash Corporation)) (approximately 12% solids), the composition was spread into a flat sheet approximately 3 mm thick. This was then sandwiched between two sheets of wicking material, such as a paper towel. The entire composition was then placed in a 30 ton hydraulic press and subjected to 60,000 lbf for 15 minutes. The sheet was removed and a thickness of approximately 0.2 mm was noted. Additionally, the material had expanded radially 200-300%. The material was crosslinked using 50 mM EDC (pH 5.4) in water. The sheet was soaked overnight in the solution and then serially rinsed 3× for 2 hours with agitation in water. This was then allowed to air dry.

Thus since the invention disclosed herein may be embodied in other specific forms without departing from the spirit or general characteristics thereof, some of which forms have been indicated, the embodiments described herein are to be considered in all respects illustrative and not restrictive, by applying current or future knowledge. The scope of the invention is to be indicated by the appended claims, rather than by the foregoing description, and all changes which come within the meaning and range of equivalency of the claims are intended to be embraced therein.

What is claimed is:

1. An implantable device comprising (i) a carrier solvent: (ii) a lubricant comprising collagen dissolved in said carrier solvent, and (iii) a structure comprising polymer fibers that are at least partially aligned, wherein said alignment of said fibers expresses itself as an architecture comprising a plurality of plates, each of said plates comprising aligned polymer fibers, said plates defining at least one space therebetween comprising fluid planes, said fluid planes existing as multiple fissures located randomly within the structure, further wherein said architecture is present throughout said structure, and further wherein said implantable device is arranged to be surgically implanted into a body of a living being, said device produced by a process comprising:

a) providing a mixture, said mixture comprising a plurality of fibers, said lubricant, and a suspension fluid, said suspension fluid filling a void space between said fibers;

b) subjecting said mixture to at least one compressive force of a magnitude of at least 0.2 ton per square inch and not more than 100 tons per square inch, said compressive force causing the migration and at least partial alignment of said fibers as said suspension fluid moves outward from a direction of said compression; and c) removing at least a portion of said suspension fluid from said mixture.

2. The implantable device of claim 1 further comprising at least one reinforcing element.

3. The implantable device of claim 2, wherein said at least one reinforcing element is selected from the group consisting of particulates, threads, fibers, whiskers, textiles, rods, meshes, and combinations thereof.

4. The implantable device of claim 1 further comprising at least one biologically active agent.

5. The implantable device of claim 2 further comprising at least one biologically active agent.

6. The implantable device of claim 1 wherein said plates of aligned fibers do not traverse the length of said device, said plates of aligned fibers being nested in a compact orientation.

7. The implantable device of claim 1 wherein said device has an anisotropic structure.

8. The implantable device of claim wherein said device has an isotropic structure in two dimensions.

9. An implantable device comprising (i) a lubricant comprising dissolved collagen and (ii) polymer fibers originally having void spaces therebetween, wherein said fibers have been compressed in at least one direction while in contact with a fluid comprising said lubricant, said lubricant serving to reduce said void space by enabling migration of said polymer fibers through said fluid as said fluid is expelled in a direction radial to said direction of compression, said lubricant furthermore enabling alignment of said polymer fibers, said alignment being expressed as an architecture comprising a plurality of plates comprising aligned fibers, and wherein said plates define at least one space therebetween comprising fluid planes, said fluid planes existing as multiple fissures located randomly within said architecture, and further wherein said polymer fibers on a periphery of said implantable device are at least partially cross-linked, and further wherein polymer fibers located away from said periphery are not cross-linked, and further wherein said implantable device is suitable for implantation into a body of a living being.

10. The implantable device of claim 9 further comprising at least one pocket located inside the cross-linked fiber periphery.

11. The implantable device of claim 10 further comprising at least one substance provided to said at least one pocket, wherein said at least one substance is selected from the group consisting of ceramics, polymers, cells, biologically active agents, liquids and combinations thereof.

12. The implantable device of claim 1, wherein the device is arranged to swell upon implantation and exposure to a bodily fluid, thereby functioning as a hemostatic tract plug.

13. The implantable device of claim 1, wherein said implantable device is arranged to accept a suture and resist tearing.

14. The implantable device of claim 1, wherein said implantable device serves a medical device function, said function selected from the group consisting of dura repair, hernia repair, rotator cuff repair, nerve repair, ligament repair, tendon repair, meniscal repair, muscle repair, sling, joint repair, spinal repair, craniofacial repair, and maxiofacial repair.

15. An implantable device comprising (i) a lubricant comprising dissolved collagen and (ii) multiple layers of non-cross-linked polymer fibers produced by a process comprising:

(a) providing a mixture of polymer fibers, said lubricant and at least one liquid, said mixture defining void spaces between said polymer fibers and liquid; and (b) compressing said mixture along at least one axis, thereby reducing an amount of said void space and facilitating migration and alignment of said polymer fibers to form fibrous plates as said fluid is expelled lateral to said axis of compressing, wherein upon compression said fibrous plates create a layered structure, wherein said layering occurs at a microscopic as well as at a macroscopic level.

16. The implantable device of claim 15, wherein the multiple layers of polymer fibers are composed of different polymers.

17. The implantable device of claim 15, wherein the multiple layers of polymer fibers form a gradient.

18. A compressed fibrous matrix wherein said matrix comprises (i) a carrier solvent: (ii) a lubricant comprising collagen dissolved in said carrier solvent, and (iii) multiple plates of oriented fibers, said multiple plates being present throughout said matrix and existing both at a microscopic as well as a macroscopic level, and further said plates being locked in a compact anisotropic structure, and still further wherein the orientation of fibers within each plate is independent of the orientation of fibers within adjacent plates, with said plates being formed by applying a unidirectional compressive force of between 0.2 and 100 tons per square inch to a fibrous dough comprising said fibers, said lubricant and a suspending fluid, said fibers being distributed in said suspending fluid, the compressive force causing said fibers to align as fluid flows away from said direction of said compressive force.

19. The matrix of claim 18 wherein said plates are oriented.

20. The matrix of claim 18 wherein said plates are aligned.

21. The matrix of claim 18 wherein said plates are randomly oriented.

22. The matrix of claim 18 wherein the fibers are composed of at least two different polymers.

23. The matrix of claim 18 wherein the fibers are contacted with a lubricant prior to said compression.

24. The matrix of claim 18 wherein the fibers are contacted with a plasticizer.

25. The matrix of claim 18 wherein the fibers are contacted with a surfactant.

26. The matrix of claim 18 wherein the plates form microscopic laminations.

27. The matrix of claim 18 wherein the matrix is cross-linked.

28. The matrix of claim 18 wherein only the outer surface of the fibrous matrix is cross-linked leaving the interior substantially un-cross-linked.

29. The matrix of claim 18 in the form of a pocket.

30. The matrix of claim 18 in the form of a tube.

31. The matrix of claim 18 wherein the fibrous matrix is compressed into a sheet.

32. The matrix of claim 18 wherein the fibrous matrix is compressed into a cylinder.

33. The matrix of claim 18 wherein the fibrous matrix is compressed into a block.

34. The matrix of claim 18 wherein the plates of the fibrous matrix create a gradient.

35. The matrix of claim 18 further containing a reinforcing material.

36. The matrix of claim 18 wherein the plates form a coating around an object.

37. The matrix of claim 18 further containing a biologically active agent.

38. The matrix of claim 18 further containing a microstructure.

39. The matrix of claim 18 further containing a particulate.

40. The implantable device of claim 3, existing as claimed at a time x, and further wherein at a time y that is earlier than time x, said implantable device further comprised at least one lubricant in contact with said fibers, and void space, and in between said time y and said time x, said implantable device was subjected to compression, whereby said lubricant served to reduce said void space by facilitating migration and alignment of said polymer fibers.

41. The implantable device of claim 9, wherein said alignment of said polymer fibers comprises alignment into a layered structure, the layering occurring at both a microscopic level as well as a macroscopic level.

42. The implantable device of claim 1, wherein said plates are aligned.

43. The implantable device of claim 1, wherein said plates are randomly oriented.

44. The implantable device of claim 1, wherein the orientation of fibers within each plate is independent of the orientation of fibers within adjacent plates.

45. The implantable device of claim 9, wherein said alignment of said fibers takes the form of a plurality of plates, the fibers within a given plate being oriented.

46. The implantable device of claim 45, wherein said plates are aligned.

47. The implantable device of claim 45, wherein said plates are randomly oriented.

48. The implantable device of claim 45, wherein the orientation of fibers within each plate is independent of the orientation of fibers within adjacent plates.

49. The implantable device of claim 9, wherein the fibers are composed of at least two different polymers.

50. The implantable device of claim 9, wherein the fibers are contacted with a plasticizer.

51. The implantable device of claim 9, wherein the fibers are contacted with a surfactant.

52. The implantable device of claim 9, wherein the plates form microscopic laminations.

53. An implantable device comprising (i) a lubricant comprising dissolved collagen and (ii) a structure comprising polymer fibers that are at least partially aligned and not cross-linked, wherein said alignment of said fibers expresses itself as an architecture comprising a plurality of plates, each of said plates comprising aligned polymer fibers, said plates defining at least one space therebetween comprising fluid planes, said fluid planes existing as multiple fissures located randomly within the structure, and further wherein said implantable device is arranged to be surgically implanted into a body of a living being.

54. The implantable device of claim 15, wherein said mixture is not constrained lateral to the compression direction.

55. The implantable device of claim 1, wherein said mixture is not constrained lateral to the compression direction.

56. The implantable device of claim 1, wherein said suspending fluid comprises water.

57. The implantable device of claim 1, wherein said carrier solvent comprises at least one of water, alcohol and acetone.

\* \* \* \* \*